(12) United States Patent
Yamazaki et al.

(10) Patent No.: US 10,451,553 B2
(45) Date of Patent: Oct. 22, 2019

(54) FLUORESCENCE SPECTROMETER

(71) Applicant: Hitachi High-Technologies Corporation, Minato-ku, Tokyo (JP)

(72) Inventors: Motohiro Yamazaki, Tokyo (JP); Yuichiro Ota, Tokyo (JP); Satoshi Takahashi, Tokyo (JP); Yoshitaka Kodama, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/129,287

(22) PCT Filed: Mar. 18, 2015

(86) PCT No.: PCT/JP2015/058022
§ 371 (c)(1),
(2) Date: Sep. 26, 2016

(87) PCT Pub. No.: WO2015/151812
PCT Pub. Date: Oct. 8, 2015

(65) Prior Publication Data
US 2017/0115223 A1  Apr. 27, 2017

(30) Foreign Application Priority Data
Apr. 3, 2014  (JP) ................. 2014-077323

(51) Int. Cl.
*G01N 21/64* (2006.01)
*G01J 3/44* (2006.01)
(Continued)

(52) U.S. Cl.
CPC ........ *G01N 21/6456* (2013.01); *G01J 3/0208* (2013.01); *G01J 3/4406* (2013.01);
(Continued)

(58) Field of Classification Search
CPC ........... G01N 21/6428; G01N 21/6452; G01N 21/6458; G01N 21/6408; G01N 21/645
See application file for complete search history.

(56) References Cited

U.S. PATENT DOCUMENTS 5,062,942 A  11/1991 Kambara et al.
5,582,705 A  12/1996 Yeung et al.
(Continued)

FOREIGN PATENT DOCUMENTS

CN  101939632 A  1/2011
EP  1 384 992 A1  1/2004
(Continued)

OTHER PUBLICATIONS

International Search Report (PCT/ISA/210) issued in PCT Application No. PCT/JP2015/058022 dated Jun. 16, 2015, with English translation (three (3) pages).
(Continued)

*Primary Examiner* — Edwin C Gunberg
*Assistant Examiner* — Mamadou Faye
(74) *Attorney, Agent, or Firm* — Crowell & Moring LLP

(57) ABSTRACT

During analysis of samples of unknown concentration, situations frequently occur in which the dynamic range is insufficient, necessitating reanalysis. Accordingly, a fluorescence spectrometer which splits a single object image into multiple images having different fluorescent intensity by means of image splitting elements, and simultaneously detects the plurality of images obtained thereby in different regions within the same detection plane, is proposed.

16 Claims, 16 Drawing Sheets

(51) Int. Cl.
  *G01N 27/447* (2006.01)
  *G01J 3/02* (2006.01)

(52) U.S. Cl.
  CPC ..... *G01N 27/447* (2013.01); *G01N 27/44721* (2013.01); *G01N 2021/6417* (2013.01); *G01N 2021/6471* (2013.01); *G01N 2201/06113* (2013.01)

(56) References Cited

U.S. PATENT DOCUMENTS

| | | | |
|---|---|---|---|
| 6,132,578 | A | 10/2000 | Kambara et al. |
| 6,485,625 | B1 * | 11/2002 | Simpson ............... B01J 19/0093 204/450 |
| 6,690,467 | B1 | 2/2004 | Reel |
| 7,390,390 | B2 * | 6/2008 | Yamamoto .......... B01L 3/50853 204/601 |
| 7,513,984 | B2 * | 4/2009 | Inaba ............... G01N 27/44782 204/452 |
| 2002/0128557 | A1 * | 9/2002 | Hohla .................. A61B 5/0084 600/476 |
| 2003/0133107 | A1 * | 7/2003 | Saito ........................ G01J 3/08 356/317 |
| 2003/0155245 | A1 | 8/2003 | Morioka et al. |
| 2005/0133373 | A1 | 6/2005 | Inaba et al. |
| 2005/0227274 | A1 * | 10/2005 | Takahashi ............... G01N 21/07 435/6.12 |
| 2010/0327184 | A1 | 12/2010 | Hayashi |
| 2012/0097864 | A1 | 4/2012 | Takahashi et al. |
| 2012/0126142 | A1 * | 5/2012 | Matsui ............... G01N 21/6452 250/459.1 |
| 2012/0184813 | A1 * | 7/2012 | Terakawa ........... A61B 1/00009 600/109 |
| 2013/0100443 | A1 * | 4/2013 | Li ..................... G02B 27/1006 356/317 |

FOREIGN PATENT DOCUMENTS

| | | |
|---|---|---|
| JP | 10-19845 A | 1/1998 |
| JP | 2011-27706 A | 2/2011 |
| WO | WO 01/84134 A1 | 11/2001 |
| WO | WO 2010/150468 A1 | 12/2010 |

OTHER PUBLICATIONS

Chinese-language Office Action issued in counterpart Chinese Application No. 201580010323.1 dated Mar. 14, 2018 (seven pages).

* cited by examiner

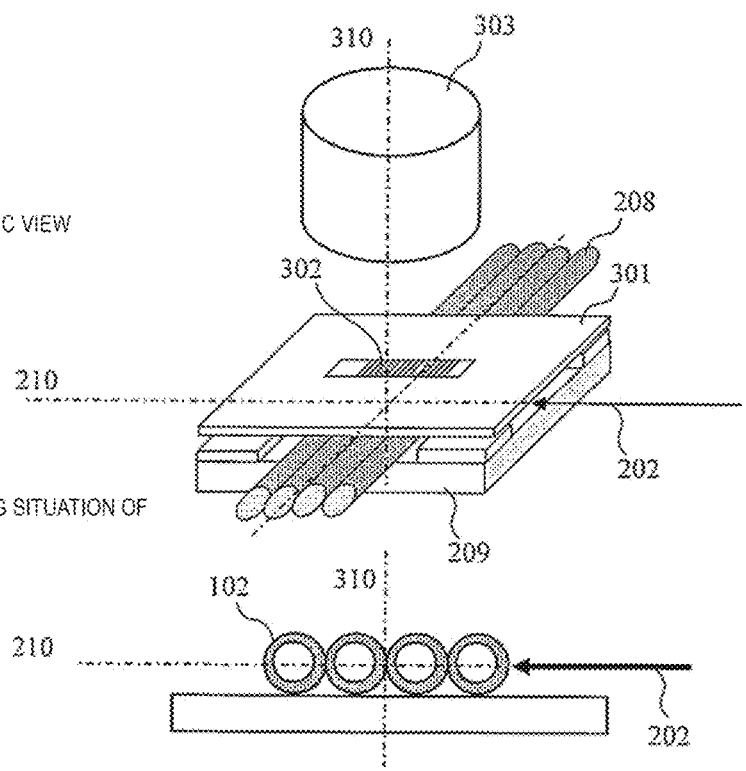

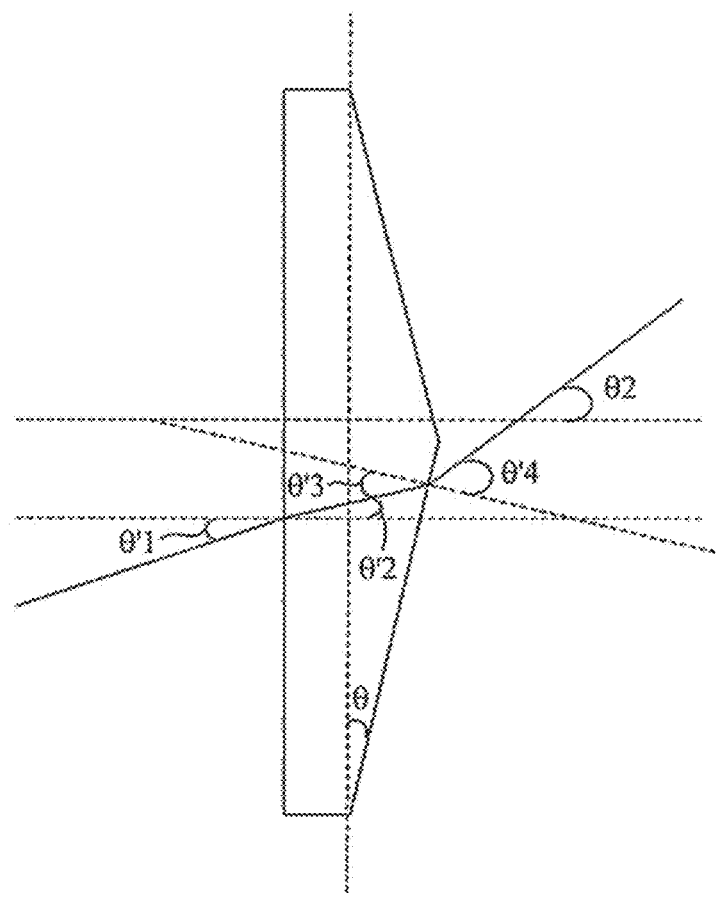

FLUORESCENCE SPECTROMETER

TECHNICAL FIELD

The present invention relates to a fluorescence spectrometer used for analyzing a nucleic acid or protein.

BACKGROUND ART

As one of the fluorescence spectrometers, a capillary electrophoretic apparatus is exemplified. The capillary electrophoretic apparatus is mainly used for determining a base sequence or a base length of DNA. In capillary electrophoresis, a thin tube which is referred to as a capillary is filled with a migration medium such as a gel and a DNA fragment of a sample is migrated within this capillary. In addition, the time required for the sample to finish migration of only a constant distance (normally, from one end of the capillary to the other end) is measured so as to investigate the length of the DNA fragment. Each sample, in other words, each DNA fragment, is labeled by a fluorescent pigment, and a fluorescent signal of the migrated sample is detected by means of an optical detector placed at the terminal of the capillary.

A multi-focus system disclosed in PTL 1 is exemplified as one of systems of irradiating a plurality of capillaries with a laser beam. In this system, a capillary positioned on one end or both ends of a capillary array configured to include the plurality of capillaries arranged on a planar substrate is irradiated with a laser beam. In addition, the radiated laser beam propagates capillaries adjacent to each other one by one to traverse the capillary array. Light emission caused in the capillary array is detected by a photodetector. A sample including DNA labeled by a fluorescent pigment is introduced into the capillary, and the sample is irradiated with a laser beam such that the laser beam propagates the plurality of capillaries arranged in a row. The DNA which is fluorescence-labeled by the laser beam radiated to the capillary emits fluorescent light. By measuring the fluorescent light from each capillary, it is possible to analyze DNA of the sample introduced into each capillary. The same applies to a case of analyzing protein, or the like.

In the fluorescent light detection of the apparatus described above, the fluorescent light in each fluorescent pigment obtained by irradiating the terminal of the capillary with a laser beam having a specific wavelength is separated by means of a diffraction grating, and an image in a space direction and a wavelength direction is detected by a two-dimensional detector such as a CCD. An image captured by the detector is stored as spectral data of a specific capillary, and used for data analysis. A fluorescence spectrometer disclosed in PTL 2 continuously scatters the obtained fluorescent light using a diffraction grating, and performs analysis by measuring a spectrum (in actuality, discrete for every pixel).

Currently, the use of an analyzer using a fluorescence detector has been extended from a research market to an application market, and it is necessary to cope with a sample having different concentration (detection intensity is varied). The above-mentioned capillary electrophoretic apparatus is one of the above. A major fluorescence detector which has been used in the related art detects the fluorescent light by a single detector. A dynamic range or a detection range of the detector depends on excitation efficiency of a fluorescent sample, a NA of a camera lens, or performance of a two-dimensional detector.

In a device in which a wide dynamic range or a detection range is necessary, a method is used, in which a beam splitter or a filter is provided in the middle of an optical path to split a detection image and a plurality of images having different fluorescent intensity is obtained by a plurality of detectors. However, since a plurality of expensive detectors is necessary, there is a demerit such as an increase in cost of the apparatus and an increase in size of a detection unit.

In addition, the fluorescent intensity depends on the irradiation detection time or the irradiation intensity. Therefore, it is possible to obtain data having different intensity by controlling a parameter of an irradiation side. Thus, a method is suggested, in which the period of the irradiation time or the detection time is elongated or reduced during analysis of using a single detector so as to obtain data having different fluorescent intensity. However, in an apparatus in which data is obtained in times series, measured points per a unit time may be reduced and sampling points necessary for obtaining data may be insufficient.

CITATION LIST

Patent Literature

Patent Document 1: U.S. Pat. No. 5,582,705
Patent Document 2: U.S. Pat. No. 6,690,467

SUMMARY OF INVENTION

Technical Problem

In the following, a problem of the related art, which has been determined as a result of thorough study of the present inventors, will be described.

Normally, in the capillary electrophoretic apparatus, a sample in which a DNA amount is adjusted is analyzed. However, from now on, it is expected that the use of the capillary electrophoretic apparatus will be extended to an application market such as clinical diagnosis, DNA identification, or the like. In this case, it is considered that an ability of coping with a sample having an unknown concentration is required in the capillary electrophoretic apparatus. However, in a case where the dynamic range is insufficient, it is considered that in analysis of the sample having a high concentration, a detection signal value is saturated, and in analysis of the sample having a low concentration, the detection signal cannot be detected frequently. In this case, an analyst needs to re-adjust the concentration and then to perform analysis again.

For example, in the method disclosed in PTL 1, since the plurality of samples is measured simultaneously, the concentration of the sample is limited within the dynamic range of the apparatus. Normally, in a gene sequencing analysis using electrophoresis, the concentration of the sample is adjusted to be almost uniform by taking time for purifying the sample in a pre-treatment step of the electrophoresis, and then the analysis is performed. For example, the concentration is checked by means of RNA, and then the sample is applied to the electrophoretic apparatus.

However, if the current electrophoretic apparatus is applied to the field of clinical analysis of the function of genes, a sample which has not gone through the pre-treatment step sufficiently becomes a measurement target. For example, in checking the concentration, a sample in a small amount which is directly applied to the electrophoretic apparatus without confirming the concentration, or a sample of which the concentration is made to be high in advance for analyzing expression becomes a measurement target as well. In this case, a measurement signal value during the analysis may exceed the range of the detection limit. Therefore, the analyst adjusts a voltage and time at the time of injecting the sample and controls the injection amount of the sample to perform analysis again.

In addition to the above, as an actual analysis method, a method is exemplified, in which the irradiation time of excitation light is set to two ways and the irradiation time having unsaturated signal intensity is used for the analysis. However, setting the irradiation time to two ways during the sampling time may not secure data processing and the transmitting time sufficiently. For example, in a case where the sampling time is 150 milliseconds, if 40 milliseconds is provided for one data process, a total 70 milliseconds is merely secured by setting the irradiation time to two ways. In a case where 100 milliseconds is required as the irradiation time of the excitation light in order to secure the original sensitivity, it is understood that this method is not proper. Also, a method is exemplified, in which two detectors are provided to measure the irradiation time of the excitation light to two ways, but the cost of the apparatus becomes expensive.

Solution to Problem

In order to solve the aforementioned problem, in a fluorescence spectrometer according to the present invention, a method is suggested, in which one object image is split into a plurality of images having different fluorescent intensity by means of image splitting elements and the obtained plurality of images are detected simultaneously in different regions within the same detection plane.

Advantageous Effects of Invention

According to the present invention, since a signal having different fluorescent intensity is measured simultaneously with respect to the same sample, externally, it is possible to increase a dynamic range. A problem, configuration, and effect other than the above will be clarified in the description of the embodiment below.

BRIEF DESCRIPTION OF DRAWINGS

FIGS. 3A and 3B are views illustrating a schematic configuration of a fluorescence spectrometer of the electrophoretic apparatus used in Example 1.

FIG. 6C is a view describing elements of an image splitting prism.

DESCRIPTION OF EMBODIMENTS

Figure 1:
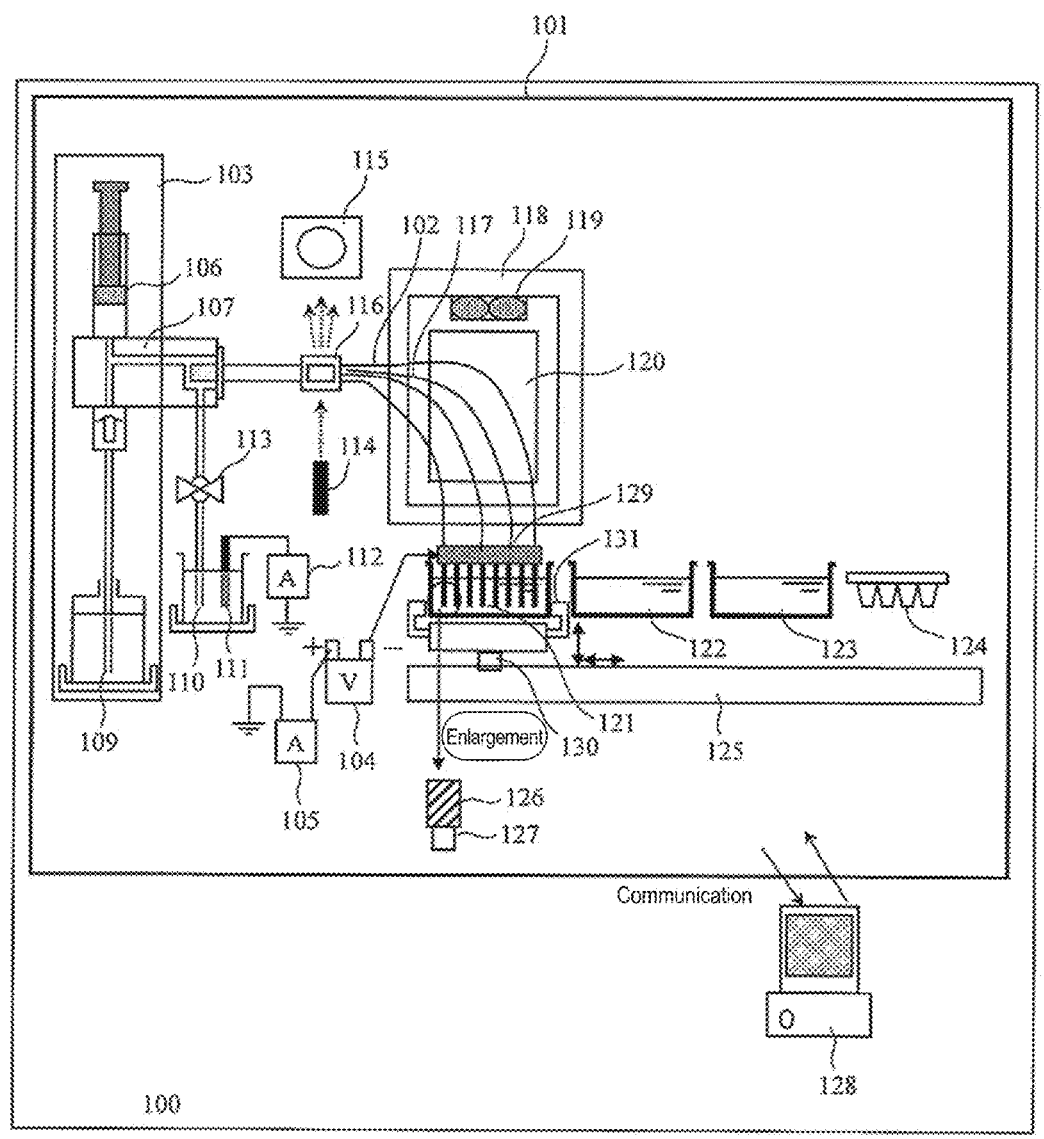
FIG. 1 is a view illustrating a schematic configuration of a gene analysis apparatus used in each Example.

First, a schematic configuration of the fluorescence spectrometer mentioned in each Example below will be described. All of the fluorescence spectrometers mentioned in each Example below are common to each other in that one object image is split into a plurality of images having different fluorescent intensity by means of an image splitting element, and the obtained plurality of images are detected simultaneously in different regions within the same detection plane. In addition, the fluorescence spectrometer is used by combining the image splitting element and the light dispersing element.

In all of the fluorescence analysis apparatuses, since a plurality of signals having different fluorescent intensity is measured simultaneously with respect to the same sample, it is possible to increase a dynamic range externally. For example, two types of strong and weak images having signal intensity 10 times different from each other can be obtained and samples having concentration 10 times different from each other can be analyzed. For example, in a case of a sample having high concentration, since the fluorescent intensity is strong and an image on the detector is saturated, an accurate analysis may not be performed. In this case, the analysis is performed by using an image on a side of having weak fluorescent intensity. In a case of a sample having high concentration, the analysis is performed by using an image having strong fluorescent intensity. Even if the concentration is different 10 times, the analysis can be performed by using two strong and weak data on the detector differently.

The fluorescence detector is configured to include an optical filter for separating excitation light and fluorescent light, a condensing lens for obtaining an image, a light dispersing element for dispersing the fluorescent light (a diffraction grating, a prism, or an optical filter), an optical element for splitting the image (a prism, a beam splitter), an image forming lens, and a two-dimensional detector for obtaining a dispersed light image as data (a CCD, a CMOS, or the like).

The optical filter is disposed between an object surface and the condensing lens and behind the condensing lens. In addition, the light dispersing element for dispersing the fluorescent light and the optical element for splitting the image are disposed on an optical path collimated behind the condensing lens. An image forming lens is disposed on an optical path after light dispersing and image splitting and in front of the two-dimensional detector.

The structure of the image splitting element used for splitting an image (for example, a prism) is configured to include a plane surface perpendicular to an optical axis (optical path) of the collimated fluorescent light and a plane surface in the same number as the number of splitting the optical path. The surface splitting the image is inclined by number of several degrees to tens of degrees rather than a surface parallel to the plane surface perpendicular to the optical axis of the collimated fluorescent light. For example, the surface splitting the image is inclined in the range of 1° to less than 20°. Accordingly, the optical axis is changed on the image splitting surface of the prism. As a plurality of fluorescent light paths is generated in the number of the image splitting surface, the image is split. If a dielectric film or a vapor deposited film is formed on each split surface to vary transmittance, the fluorescent intensity of the split image can be controlled. In addition, by changing the ratio of the area of each split surface, the fluorescent intensity of each image can be controlled.

An image splitting element having a different structure (for example, a beam splitter) has a flat plate shape, and splits the optical path by transmission and reflection. The ratio of transmission to reflection can be controlled. The image splitting element is disposed with an inclination of 45° to the optical axis of the collimated fluorescent light. Since the transmission optical axis and the reflection optical axis form a great angle of 90°, a total reflection type mirror is disposed on the transmission optical path or the reflection optical path, and is almost parallel to the split optical path.

Hereinafter, the mechanism of the image splitting and image forming of a plurality of images within the fluorescence spectrometer will be described. Even in a case of the fluorescence spectrometer according to each Example, a laser beam is radiated to the capillary, or the like to excite a fluorescent pigment in the sample in the same manner as the related technology. The fluorescent light, necessary for the analysis is transmitted while the excitation light component of the excited fluorescent light is prevented by the optical filter, or the like, the fluorescent light is condensed by a lens and collimated. The unnecessary component is removed by the optical filter again from the collimated fluorescent light and the light is dispersed by the diffraction grating. The light dispersed by the diffraction grating is divided into the 0-order light, the $1^{st}$-order light, and the $2^{nd}$-order light component. In the fluorescence spectrometer according to Example, the image splitting element is disposed on the optical path of the $1^{st}$-order light having the highest signal intensity after light dispersing. The light dispersed by the diffraction grating is retained to be in a collimated state.

In an image splitting prism, the optical axis passes through a prism surface perpendicular to the optical axis and is changed on the surface not parallel to the prism surface but the surface inclined by several degrees rather than the parallel surface. The light is refracted on the interface between the prism and the air according to Snell's Law. If there is a plurality of surfaces inclined, the new optical path is generated in the number of the surfaces, and one image incident on the prism is split so as to form a plurality of images. At this time, if the dielectric film is vapor-deposited on each surface used for image splitting, and transmittance is controlled, it is possible to split the image into an image having different signal intensity.

Finally, the dispersed light and the fluorescent light split into the plurality of images, in other words, the plurality of optical paths are image formed by the two-dimensional detector using a camera lens, or the like. A plurality of split objects and light dispersed images are formed on the two-dimensional detector. When the light is split into a plurality of optical paths, the signal intensity of the formed image is determined depending on the amount of light of the split surface. In addition, as described below, the detector is not limited to the two-dimensional detector and a one-dimensional detector is used according to a combination of the image splitting element and the light dispersing element to be used.

Hereinafter, examples will be described by referring to the attached drawings. However, it is noted that the examples are merely one example to execute the present invention and do not limit the technical scope of the present invention. In addition, the same reference numbers are attached in the common configuration in each drawing.

Example 1

FIG. 1 illustrates a schematic configuration of a gene analysis apparatus in which the capillary electrophoretic apparatus is used for fluorescent light detection. In addition, the configuration of the apparatus is common in each Example described below. The gene analysis apparatus is one example of the fluorescence spectrometer.

A gene analysis apparatus 100 is configured to include a data analysis apparatus 128 and an electrophoretic apparatus 101. The electrophoretic apparatus 101 is configured to include a detection unit 116 for optically detecting a sample, a thermostatic bath 118 for retaining the temperature of a capillary constantly, a conveyer 125 for transporting various containers to a capillary cathode end, a high voltage power supply 104 for adding high voltage to the capillary, a first ammeter 105 for detecting an electric current generated from the high voltage power supply, a second ammeter 112 for detecting an electric current flowing to the electrode on an anode side, a capillary array 117 configured to include a single or a plurality of capillaries 102, and a pump mechanism 103 for injecting a polymer to the capillary.

The capillary array 117 is an exchange member including a plurality of (for example, 4) capillaries, and includes a road header 129, a detection unit 116, and a capillary head. In a case where a measurement method is changed, the capillary array 117 is repositioned to adjust the length of the capillary 102. In addition, when a damage or deterioration in quality of the capillary is observed, the capillary array is replaced with a new capillary array.

The capillary 102 is configured of a glass tube having an inner diameter of tens of to hundreds of microns and an outer diameter of hundreds of microns, and the surface is coated with polyimide in order to improve strength. However, the light irradiation portion to be irradiated with a laser beam is configured such that a polyimide film is removed in order for light emission in the inside to leak to the outside easily. The interior of the capillary 102 is filled with a separation medium for imparting a migration speed difference at the time of electrophoresis. There is a separation medium having fluidity or non-fluidity but a polymer having fluidity is used in the present examples.

The detection unit 116 is a member for obtaining information depending on the sample, and the detection unit is irradiated with excitation light and emits light of a wavelength depending on the sample. The vicinity of the light irradiation portion of the four capillaries is arranged and fixed on an optically flat plane surface at the accuracy of several microns in height. At the time of electrophoresis, a substantially coaxial two laser beams are radiated from both sides and transmit all of the light irradiation portions continuously. Due to these laser beams, information light (fluorescent light having a wavelength depending on the sample) is generated from the sample and emitted to the outside from the light irradiation portions. This information light is detected by the optical detector 115 to analyze the sample.

The each capillary cathode end 127 is fixed through a hollow electrode 126 made of a metal, and the tip of the capillary is protruded about 0.5 mm from the hollow electrode 126. In addition, all of the hollow electrodes equipped in each capillary are integrally installed to a road header 129. Further, all of the hollow electrodes 126 is electrically conductive to a high voltage power supply 104 mounted to an apparatus main body, and operated as a cathode electrode when it is necessary to apply a voltage such as electrophoresis, introduction of the sample, or the like.

The capillary cathode end 127 and the capillary end (the other end) on the opposite side are tied as one by the capillary head, and are detachable from a block 107 at voltage resistant density as the tie through the capillary head. A syringe 106 is connected to one flow channel within the block 107 and the capillary is filled with a new polymer from the other end side by this syringe 106. The filling of the polymer in the capillary is executed every time of measurement, in order to improve measurement performance.

The pump mechanism 103 is configured to include the syringe 106 and a mechanism system for adding pressure to the syringe. In addition, the block 107 is a connection member for communicating with the syringe 106, the capillary array 117, an anode buffer container 110, and a polymer container 109 respectively. The optical detection unit is configured to include a light source 114 for irradiating the detection unit 116 and an optical detector 115 for detecting light emission within the detection unit 116. When the sample in the capillary separated by electrophoresis is detected, the light irradiation portion of the capillary is irradiated by the light source 114 and light emission from the light irradiation portion is detected by the optical detector 115.

The thermostatic bath 118 is coated with an insulating material in order to retain the temperature within the thermostatic bath constantly, and the temperature is controlled by a heating and cooling mechanism 120. In addition, a fan 119 causes air within the thermostatic bath to be circulated and stirred, and the temperature of the capillary array 117 is retained to be positionally uniform and constant. The conveyer 125 includes three electric motors and a linear actuator and can be movable in three axes (vertical, horizontal, and depth directions). In addition, at least one or more containers can be placed on a movable stage 130 of the conveyer 125. Further, an electric grip 131 is included in the movable stage 130 and each container can be gripped or released. Therefore, the conveyer 125 can transport a cathode buffer container 121, a cleansing container 122, a waste liquid container 123, and a sample container 124 to the cathode end by using the grip 131, if necessary. In addition, an unnecessary container is stored in a predetermined accommodation place within the apparatus.

The electrophoretic apparatus 101 is used in a state where the apparatus is connected to a data analysis apparatus 128 by a communication cable. An operator can control a function possessed by the apparatus by means of the data analysis apparatus 128 and give and receive data detected by the detector within the apparatus.

Figures 2A, 2B:
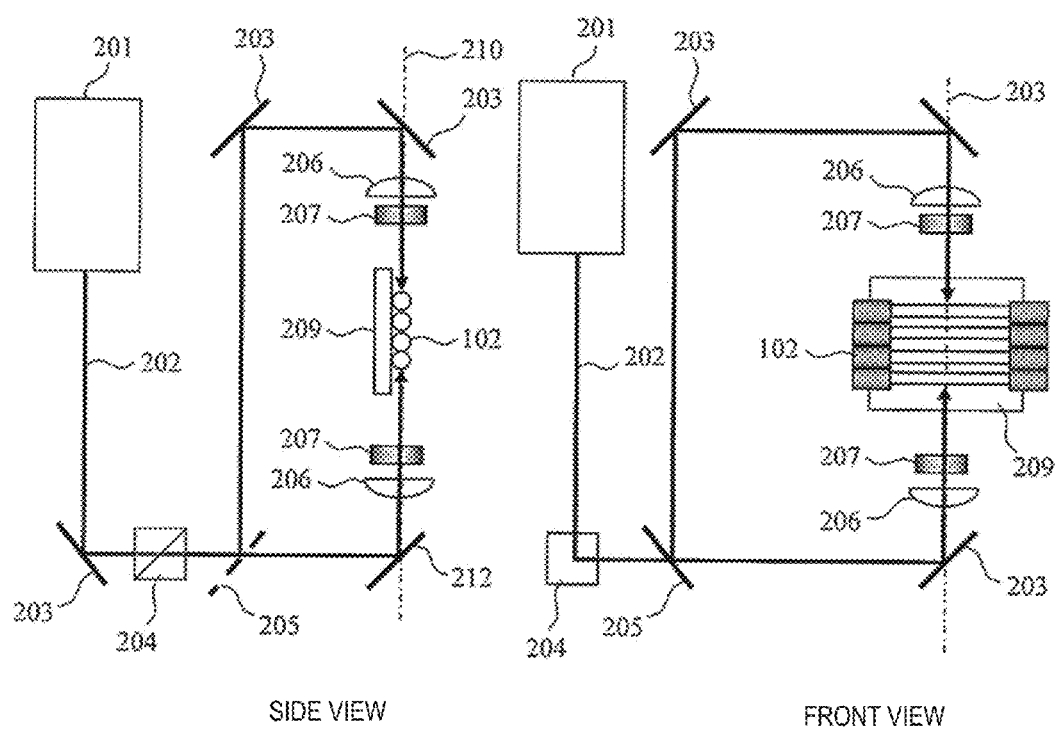
FIGS. 2A and 2B are views illustrating a schematic configuration of an irradiation unit of an electrophoretic apparatus used in Example 1.

FIG. 2 schematically illustrates configurations of an optical system laser irradiation unit of the gene analysis apparatus 100 and the vicinity of the detection unit of the capillary array 117, and an introduction path of the laser beam. A shutter for a laser, a filter, or the like is a well-known matter in the technical field and is not a direct target of the present invention. Thus, the shutter for a laser, the filter, or the like is not illustrated for simplification. FIG. (a) is a schematic side view of the laser irradiation unit and FIG. (b) is a schematic front view thereof. However, a disposition relationship in FIG. (a) and FIG. (b) does not show a disposition relationship in drafting.

A laser beam 202 emitted from a solid-state laser 201, which is a light source, passes through a reflection mirror 203 or a beam splitter 205 and is radiated to the capillary array. The four capillaries 102 are arranged on a reference base 209 and fixed, which is referred to as a capillary array. A plane surface in which a central axis of the four capillaries 102 is formed on the reference base 209 and a virtual plane in which the plane surface is extended to a whole space are referred to as a capillary-arranged plane. In addition, in the capillary-arranged plane, a virtual linear line which is perpendicular to the axis of the four capillaries and penetrates the center of the detection unit is, hereinafter, referred to as an irradiation optical axis basic axis 210.

The laser beam 202 introduced from the both ends of the capillary array is parallel to the capillary-arranged plane and is the same axis as the irradiation optical axis basic axis 210. The capillary 102 is formed such that a quartz glass tube is coated with a polymer thin film. (polyimide), but in the detection unit, the polymer coating film is removed and the quartz is uncovered. The inner diameter/outer diameter of the quartz tube are 50/320 μm, and the outer diameter of the capillary including the polymer thin film is 363 μm. The pitch of the capillary 102 is 363 μm, which is equal to the outer diameter of the capillary, and the width of the capillary array is 8.7 mm (=363 μm×4).

The laser beam 202 is irradiated to the fluorescence detection unit (portion where the quartz is uncovered) of the capillary array from one side surface of the array, and the fluorescent light emitted from the detection unit is observed so as to detect DNA. The laser beam 202 is condensed by a laser condensing lens 206 (f=60 mm). A capillary 102 positioned at the end of the capillary array and with the laser introduced thereto is, hereinafter, referred to as a first capillary. The distance between the laser condensing lens 206 and the first capillary is 62 mm, and the laser beam introduced into the first capillary propagates the capillary adjacent thereto one by one and traverse four capillaries.

Before the laser beam 202 reaches the capillary 102, a wavelength plate (λ/4) 207 is disposed at both ends of the capillary array in order to change linearly polarized light of the laser beam 202 to circularly polarized light. The laser beam 202 which has been changed to the circularly polarized light by the wavelength plate 207 on one side is changed to the linearly polarized light again by the wavelength plate 207 on the other side. At this time, a linearly polarized light direction of the linearly polarized light which has passed through the wavelength plate 207 twice is rotated 90 degrees with respect to the initial linearly polarized light direction before being introduced to the wavelength plate 207. In addition, a polarizer 204 is disposed immediately after the solid-state laser 201 as a countermeasure of the return light. The polarizer 204 is an optical element which transmits only the polarized light in one direction such as a polarizing plate or a polarized cube. Since the laser beam which has passed through the wavelength plate 207 twice is blocked by the polarizer 204, the laser beam does not reach the light source.

A disposition of an irradiation portion and the detection unit will be described using FIG. 3. As described above, a plurality of capillaries 102 (for example, four) is arranged and fixed on the reference base 209 made of ceramics, which is a plane surface, to form a capillary array. In the illustrated Example, four capillaries 102 are arranged on a capillary retention surface, pressed by a flat plate mask 301 made of silicon, and fixed by an adhesive to form a capillary array.

A plane surface in which a central axis of four capillaries is formed on the reference base 209 and a virtual plane in which the plane surface is extended to a whole space are referred to as a capillary-arranged plane. In addition, a linear line perpendicular to the irradiation optical axis basic axis 210 and perpendicular to the capillary-arranged plane is referred to as a detection optical axis basic axis 310. The laser beam 202 introduced from the both ends of the capillary array is parallel to the capillary-arranged plane and is the same axis as the irradiation optical axis basic axis 210. Every one of the capillary 102 is formed such that a quartz glass tube is coated with a polymer thin film, but in the laser irradiation unit 302 (detection portion), the polymer coating film is removed and the quartz is uncovered.

FIG. 3(b) illustrates a schematic view of the cross section in which a part of the detection unit is cut along the surface orthogonal to the capillary. There are four capillaries 102, and first, if the capillary 102 at the first end is irradiated with the laser beam 202 and the beam passes through the capillary, the next capillary 102 is irradiated. In this way, the laser beam 202 passes through a plurality of capillaries one by one and comes out from the capillary 102 at the opposite end. Since the capillary 102 has a cylindrical shape and the inside thereof is filled with a polymer, the capillary provides a condensing function which is the same as that of a convex lens. This prevents the laser beam 202 from being diverged. By irradiating the capillary with the laser beam 202 from the both right and left directions of the capillary array, it is possible to irradiate substantially all of the capillaries 102 with the laser beam 202 having uniform intensity. Therefore, it is possible to irradiate four samples simultaneously while the laser intensity s retained. A fluorescence detector 303 is disposed on a detection optical axis basic axis 310 and can simultaneously condense the fluorescent light of the four samples more effectively. In other words, all of the samples can be simultaneously detected while high sensitivity is retained.

Figures 4A, 4B:
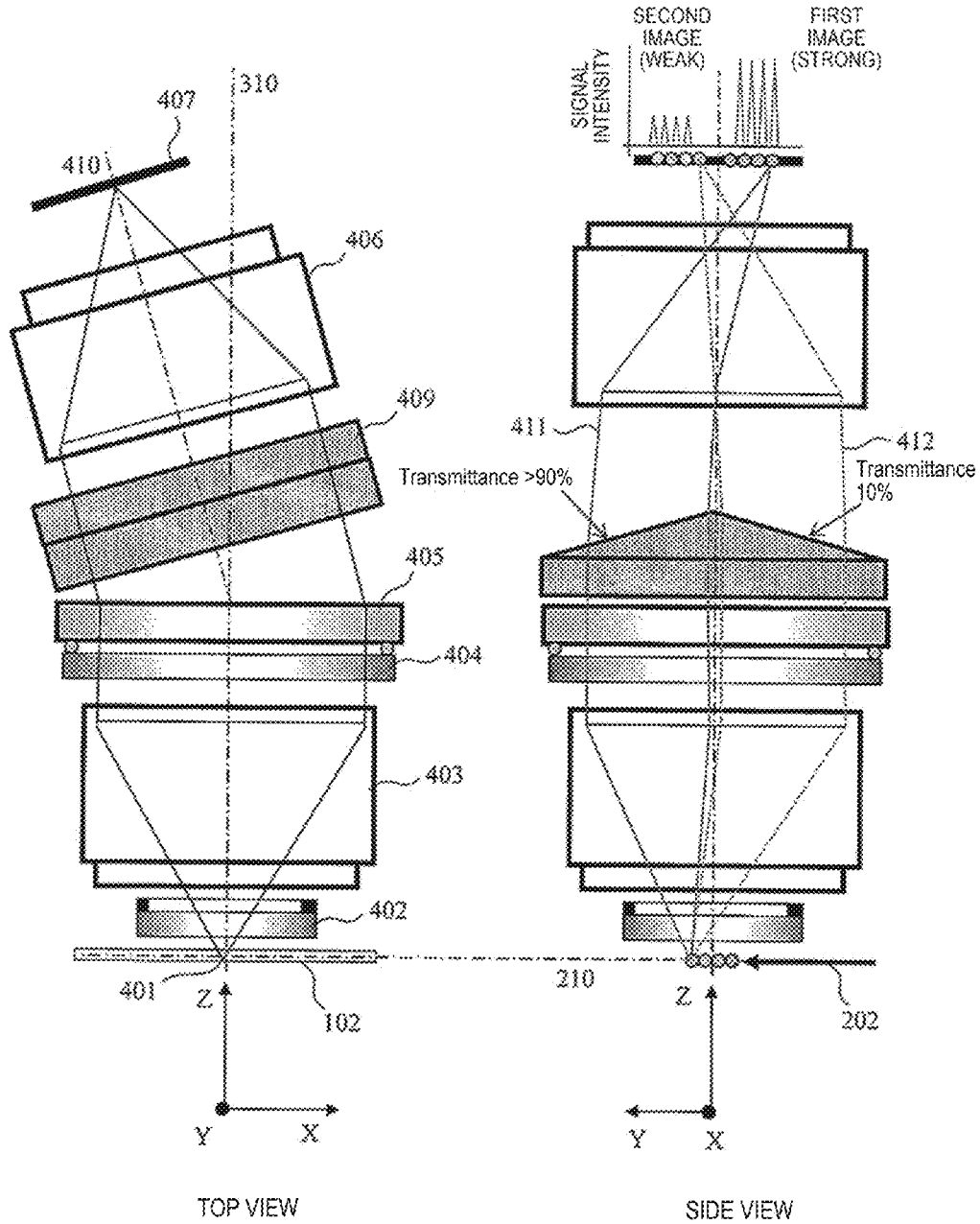
FIGS. 4A and 4B are views illustrating a detailed configuration of the fluorescence spectrometer used in Example 1.

FIG. 4 illustrates a detailed configuration of the fluorescence detector 303. FIG. 4(a) illustrates a view of the surface created by the axis of the capillary 102 and the detection optical axis basic axis 310, and FIG. 4(b) illustrates a side view thereof, that is, a view of the plane surface created by the irradiation optical axis basic axis 210 and the detection optical axis basic axis 310. However, in FIG. (b), in order to facilitate the description, a disposition of the optical system after the diffraction grating 405 is modified. Originally, it is necessary to present the disposition such that a thin prism (also referred to as "image splitting prism") 409 or an image forming lens 406 in FIG. (b) is inclined, in combination with the disposition of FIG. (a).

The fluorescence detector 303 is configured to include a first optical filter 402 and a second optical filter 404 for separating excitation light and fluorescent light, a condensing lens 403 for obtaining an image, a diffraction grating 405 for dispersing the fluorescent light, a thin prism 409 for splitting the image, an image forming lens 406 for forming an image, and a two-dimensional detector 407 (a CCD, a CMOS, or the like) for obtaining the dispersed light image as data.

Hereinafter, a detailed disposition of the optical element and a mechanism of image splitting and forming a plurality of the images within the detector will be described. The capillary 102 is irradiated with the laser beam 202 to excite the fluorescent pigment in the sample. The first optical filter 402, the condensing lens 403, the second optical filter 404, and the diffraction grating 405 are disposed on the detection optical axis basic axis 310. In the same manner as the related art, light emitted from the capillary 102 is separated to excitation light and a necessary fluorescent light component by the first optical filter 402, and the light is condensed by the condensing lens 403 to be collimated. The collimated fluorescent light is incident on the second optical filter 404 again and an unnecessary component is removed. The fluorescent light of which the unnecessary component has been removed is dispersed by the diffraction grating 405. The light dispersed by the diffraction grating 405 is divided into the 0-order light, the $1^{st}$-order light, and the $2^{nd}$-order light. In the present example, the optical path of the $1^{st}$-order light having the highest signal intensity after light dispersing is referred to as a detection optical axis after light dispersing 410, and the thin prism 409, which is an image splitting element, the image forming lens 406 for forming an image, and the two-dimensional detector 407 (a CCD, a CMOS, or the like) for obtaining a light dispersed image as data are disposed thereon.

The structure of the thin prism 409 is configured to include a plane surface perpendicular to the optical axis (optical path) of the collimated fluorescent light-perpendicular to the detection optical axis basic axis 310, and a plane surface in the same number as the number of splitting the optical path. The image splitting surface is inclined by several degrees to tens of degrees rather than the surface parallel to the plane surface perpendicular to the optical axis of the collimated fluorescent light (which will be described in FIG. 6 below). Therefore, the optical axis of the image splitting surface of the thin prism. 409 is changed. In the present example, the thin prism has two image splitting surfaces having equivalent areas and two fluorescent light paths 411 and 412 are generated, and accordingly the image is split. In the image splitting prism, the optical axis passes through a prism surface perpendicular to the optical axis and is changed on the surface, which is not parallel to the prism surface but inclined by several degrees rather than the parallel surface. The light is refracted on the interface between the prism and the air according to Snell's Law. If there is a plurality of surfaces inclined, the new optical path is generated in the number of the surfaces, and one image incident on the prism is split so as to form a plurality of images. As the dielectric film or the vapor deposited film is formed respectively on the split surface to vary the transmittance, it is possible to control the fluorescent intensity of the split image. In the present example, the thin prism 409 having the image splitting surface having 90% of transmittance and the image splitting surface having 10% of transmittance is disposed.

Finally, the dispersed light and the fluorescent light split into the plurality of images, in other words, optical paths are image formed by the two-dimensional detector 407 using the image forming lens 406. A plurality of object images obtained by splitting a specific dispersed light ($1^{st}$-order light) is image formed on a plurality of regions configuring the same detection plane of the two-dimensional detector 407. When the light is split into a plurality of optical paths, the signal intensity of the object image to be formed is determined depending on the amount of light of the split surface.

The fluorescent light which passes through the fluorescent light path 411 transmits the image splitting surface having 90% of transmittance, and accordingly a first image (strong) having strong signal intensity is formed on the two-dimensional detector 407. The fluorescent light which passes through the fluorescent light path 412 transmits the image splitting surface having 10% of transmittance, and accordingly a second image (weak) having weak signal intensity is formed on the two-dimensional detector 407. The ratio of the signal intensity of the first image to the second image is about 9:1, which is the same as the ratio of the transmittance. That is, data of the two types including the first image (strong) and the second image (weak) is obtained on the two-dimensional detector 407.

Figure 5:
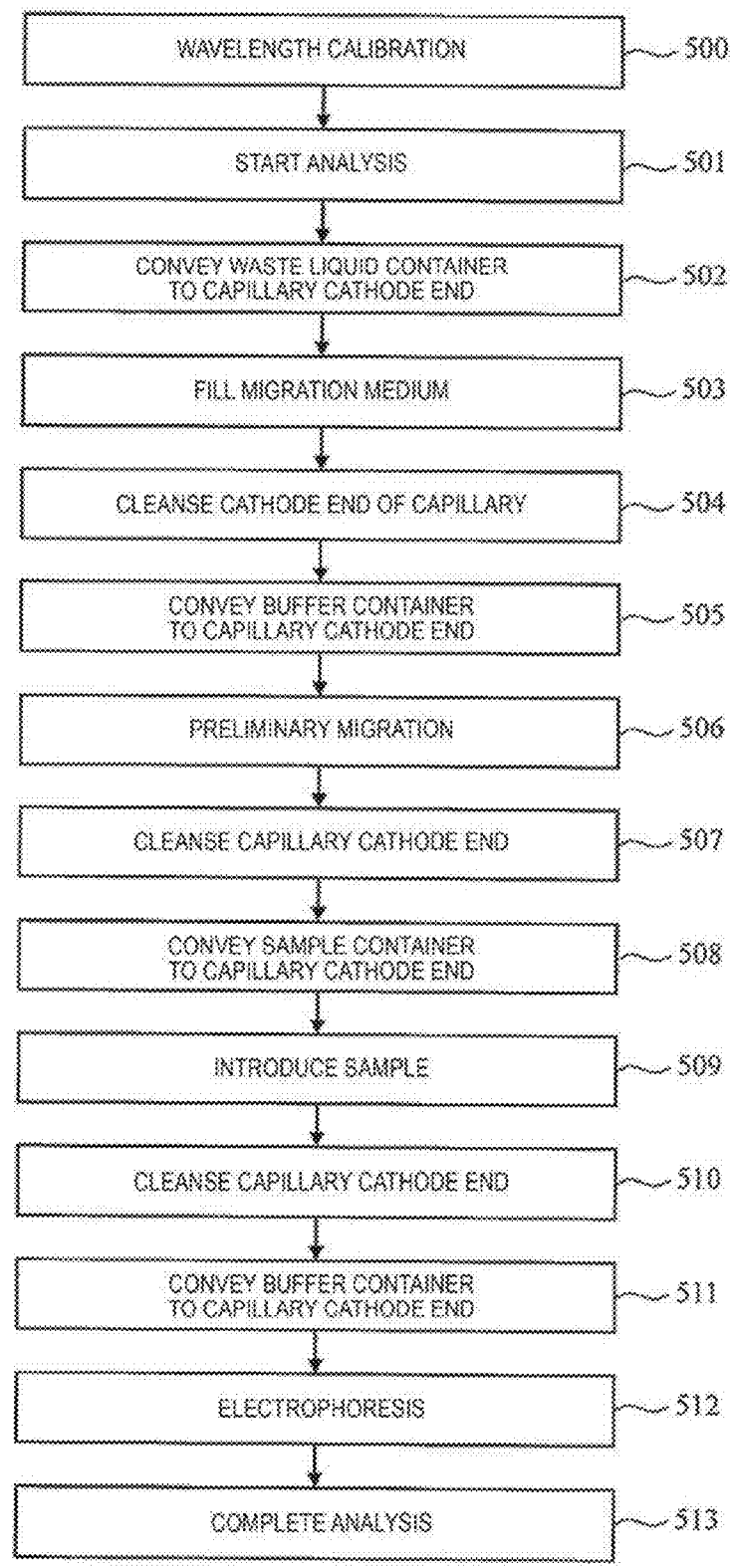
FIG. 5 is a chart illustrating a processing flow of the gene analysis apparatus used in Example 1.

Hereinafter, a basic procedure of electrophoretic analysis will be described by mainly referring to FIG. 5. Before performing the electrophoresis and analyzing an arbitrary sample, a wavelength calibration is performed every time the capillary is replaced (500). In the wavelength calibration, a well-known DNA sample calibrated from a pigment group to be analyzed, for example, four fluorescent pigments is migrated to obtain basic spectral data. In a case where analysis performance is decreased because of deterioration of the capillary 102 and the length of the capillary 102 is changed due to the analysis, the wavelength calibration is an operation that is necessarily performed after the capillary array is replaced.

The basic procedure of the electrophoretic analysis can be mainly classified into an advance preparation, filling a migration medium (503), a preliminary migration (506), an introduction of a sample (509), and analysis by electrophoresis (512). First, a preparation before starting the electrophoresis will be described. An operator sets the following into an apparatus before starting the measurement. That is, a cathode buffer container 121 containing a buffer solution, a cleansing container 122 containing pure water for cleansing capillary, a waste liquid container 123 for discharging a polymer in the capillary, a polymer container 109 containing a polymer which is a separation medium, and a sample container 124 containing a sample to be measured from now, are set.

The anode buffer container 110 is filled with a buffer which is substantially enough to sufficiently immerse both an electrode (GND) 111 and a communication tube. As the buffer solution, an electrolytic solution which is commercially available for the use of electrophoresis from each company is used. In addition, a sample which is an analysis target is dispensed to a well of the sample container 124. The sample is, for example, a PCR product of DNA. In addition, a cleansing solution for cleansing the capillary cathode end 127 is dispensed to the cleansing container 122. The cleansing solution is, for example, pure water. In addition, the separation medium for performing electrophoresis of the sample is injected within the syringe 106. The migration medium is, for example, a polyacrylamide-based separated gel (hereinafter, a polymer) which is commercially available for the use of electrophoresis from each company.

At this time, as the sample set in the sample container 124, a positive control, a negative control, and an allelic ladder are exemplified in addition to an actual sample of DNA which is an analysis target, and each sample is subjected to electrophoresis is performed in a different capillary. The positive control is, for example, a well-known PCR product including DNA, and is a sample for a control experiment for confirming that DNA is accurately amplified by PCR. The negative control is a PCR product not including DNA, and is a sample for a control experiment for confirming that an amplified product of PCR is not contaminated by an operator's DNA, a dust, or the like.

In addition, the cathode buffer container 121 is filled with a buffer which is substantially enough to sufficiently immerse the hollow electrode 126 and the capillary cathode end 127. If the measurement is started in a state where the amount of the buffer solution is insufficient or the cathode buffer container 121 is empty, there is a danger in which an electric discharge may occur between a cathode electrode having high electric potential and other electrode having low electric potential at the time of applying a high voltage. Further, a buffer level of both electrodes is preferably the same as each other. This is in order the polymer within the capillary not to move by pressure caused by a difference between the high and low electric potential. In addition, it is necessary that all of the flow channel used for the electrophoresis and the flow channel used for transporting the polymer to the flow channel are filled with a polymer before starting the measurement. Normally, in a case where the apparatus is sequentially used, the flow channel is filled with a polymer. In addition, when the polymer is substituted in the flow channel again, after replacing the capillary array and cleansing the inside of the flow channel, the operator substitutes the polymer within the flow channel again by operating the pump mechanism of the apparatus or operating the syringe manually. After that, the operator visually confirms that bubbles do not remain or foreign matters are not incorporated within the flow channel. Then, after the advance preparation is completed, the operator operates the apparatus to start the analysis. The analysis herein is analysis of adding a high voltage to an electrophoresis path.

The apparatus starts the analysis according to a command from the data analysis apparatus 128 (501). First, the apparatus prepares the injection of the polymer to the capillary and conveys the waste liquid container to the capillary cathode end by the conveyer 125 (502). After that, the apparatus injects the polymer to the capillary by the pump mechanism 103. That is, filling of the migration medium (503) is started. This step may be automatically performed after starting the analysis, or gradually, may be performed as a control signal is sent from the data analysis apparatus 128. The filling of the migration medium is a procedure that fills the inside of the capillary 102 with a new migration medium to form a migration path.

In the filling of the migration medium (503) in the present example, first, the waste liquid container 123 is conveyed right below the road header 129 by the conveyer 125 and the used migration medium to be discharged from the capillary cathode end 527 is received. In addition, the capillary 102 is filled with a new migration medium by driving the syringe 106 and the used migration medium is wasted. Finally, the capillary cathode end 127 is immersed in the cleansing solution within the cleansing container 122, and the contaminated capillary cathode end 127 is cleansed by the migration medium.

If the filling of the migration medium in a predetermined amount is completed, the conveyer 125 transports the cleansing container 122 to the capillary cathode end 127, and cleansing is performed by immersing the capillary cathode end 127 in pure water in the cleansing container (504). Next, the conveyer 125 transports the cathode buffer container 121 to the capillary cathode end 127 (505).

Next, the preliminary migration (506) is performed. This step may be automatically performed, or, gradually, performed as the control signal is sent from the data analysis apparatus 128. A predetermined voltage is applied to start the preliminary migration (506). The preliminary migration is a procedure for causing the state of the polymer within the capillary to be appropriate for the analysis, before an analysis step of the related art in which the electrophoresis is performed from the introduction of the sample. In the preliminary migration, normally, a voltage of about several kilovolts to tens of kilovolts is applied for several minutes to tens of minutes.

If the preliminary migration is completed, the capillary cathode end 127 is cleansed in the cleansing container again (507), and then the sample container 124 is transported to the capillary cathode end (508). In addition, if a voltage of about several kilovolts is applied to the capillary cathode end 127 in the sample solution accommodated in the sample container 124, an electric field is generated from the sample solution between the electrode on the anode side and the capillary cathode end. The sample in the sample solution is introduced into the capillary due to this electric field (509). If the introduction of the sample is completed, the capillary cathode end 127 is cleansed in the cleansing container (510) and then the cathode buffer container 121 is transported to the capillary cathode end 127 again (511). After that, a predetermined voltage is applied to start the electrophoresis (512).

Next, the electrophoresis (512) is performed. This step may be automatically performed, or gradually, may be performed as the control signal is sent from the data analysis apparatus 128. The electrophoresis (512) refers to that mobility is imparted to the sample in the capillary by the action of the electric field generated between the cathode and anode buffer, and the sample is separated due to the difference in mobility depending on the properties of the sample. In the electrophoresis (512) of the present example, first, the capillary cathode end 127 is immersed in the buffer solution within the cathode buffer container 121 by the conveyer 125 to form an electrification path. Next, a high voltage lower or higher than 15 kV is applied to the electrification path by the high voltage power supply 104 to generate an electric field in the migration path. Each sample component in the migration path moves to the detection unit 116 at a speed depending on the properties of each sample component due to the generated electric field. That is, the sample component is separated by the difference in the mobility speed of the component. Also, the sample component reached to the detection unit 116 is detected in an order.

For example, in a case where the sample includes a plurality of DNAs having a different base length, a difference in the mobility speed occurs due to the base length, and the DNA having a short base length reaches the detection unit 116 first. A fluorescent pigment depending on a terminal base sequence thereof is attached to each DNA. If the detection unit 116 is irradiated with excitation light from the light source 114, information light (fluorescent light having a wavelength depending on the sample) is generated from the sample and emitted to the outside. This information light is detected by the optical detector 115. During migration analysis, in the optical detector 115, this information light is detected at a constant time interval and image data is sent to the data analysis apparatus 128. Or, in order to reduce the amount of information to be sent, not the image data but only the luminescence of a part of the region in the image data may be sent. For example, only a luminance value of a wavelength position at a constant interval may be sent to each capillary. Finally, if predetermined time is elapsed from the start of applying the voltage and the expected data is obtained, the application of the voltage is stopped and the electrophoresis is finished (513). The above is a series of the measurement sequence.

Figure 6A:
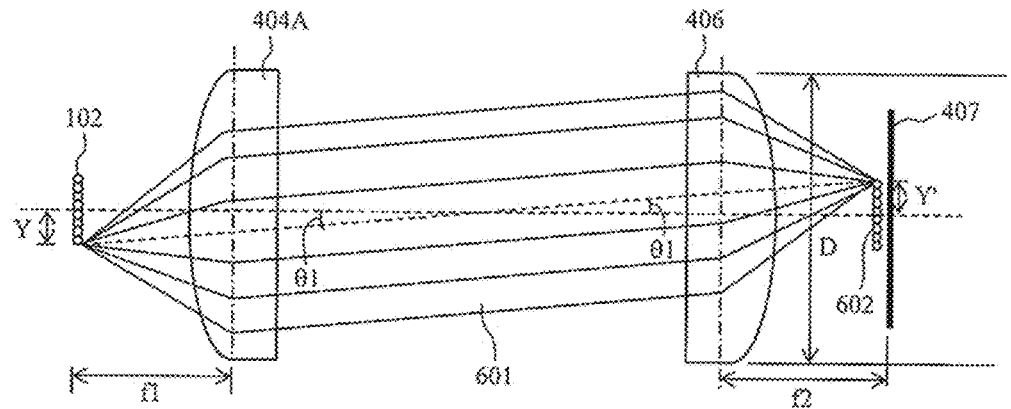
FIG. 6A is a view illustrating light ray tracing in an image forming system of the related art.
Figure 6B:
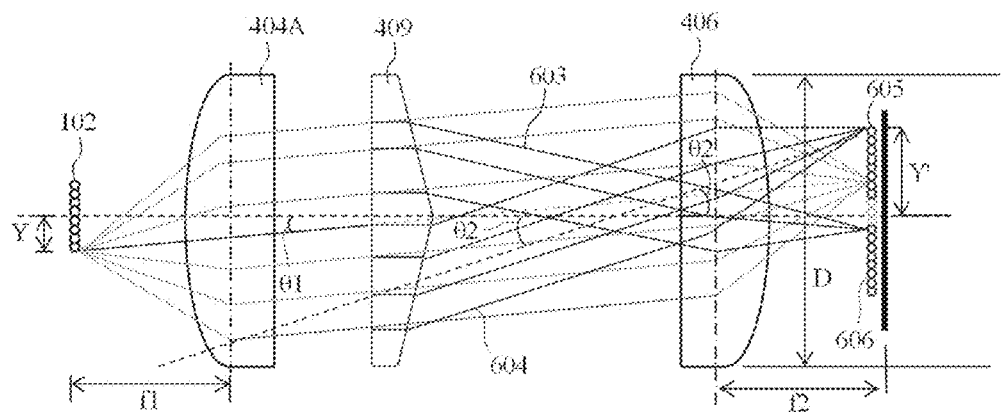
FIG. 6B is a view illustrating light ray tracing in an image forming system according to examples.

A principle in which two strong and weak images are split and a structure of the image splitting prism will be described using FIGS. 6A to 6C. In FIG. 6A to 6B, the effect of dispersing the light by the diffraction grating 405 is omitted and an image forming system is simply illustrated. FIG. 6A illustrates an image forming system by a fluorescence spectrometer according to a technology of the related art. The capillary 102 is arranged, and in a light ray tracing 601 of the fluorescent light collimated by a second condensing lens 404A, one image 602 is formed on the two-dimensional detector 407 by the image forming lens 406. In a case of the image forming system of 1:1, an image same as the object image is formed.

FIG. 6B illustrates a light ray tracing off the present example. In a case of the present example, an image splitting prism 409 is disposed in addition to a configuration of the fluorescence spectrometer of the related art. The fluorescent light having transmitted this image splitting prism 409 is refracted at an interface between the image splitting surface of the image splitting prism 409 and air. Since there are two split surfaces, the light ray is refracted. In two directions from one point, thereby forming two light ray tracing 603 and 604. Each tracing forms two images 605 and 606 by the image forming lens 406.

Hereinafter, an angle of the light ray emitted from the image splitting prism 409 or a prism design for causing the two images not to be overlapped will be described. Each subscript indicates the following values.

f1: Focal distance of condensing lens
f2: Focal distance of image forming lens
Y: Height of image (object surface) (half of array width)
Y': Height of image (image formed surface)

Next, an angle to the condensing lens is defined as follows.

θ1: Incidence angle to condensing lens
θ'1: Incidence angle to prism
θ2: Emission angle from prism
θ: Inclination angle of prism (vertical angle=2π−2θ)

First, the height of the image (image formed surface) Y' is calculated. Y' is given by the following equation.

$$Y'=\tan θ2 \times f2/f1 \times f2$$

It is necessary to satisfy a condition of the following equation such that the two split images do not overlap each other.

$$\text{Tan } θ2 \times f2 = Y' > 2Y \qquad \text{Equation (1)}$$

(However, in a case of an 1:1 image forming system in which f1=f2)

In addition, since Y/f1=tan θ1, θ1 is given by the following equation.

$$θ1=\tan^{-1}(Y/f1)$$

Here, if a refractive index of a prism material is n and an angle of the optical path within the prism is θ3 to θ4 (refer to FIG. 6C), a relationship between θ1 and θ2 satisfies the following equation according to Snell's Law.

$$n \times \sin θ'2 = \sin θ1$$

Further, the following equation is satisfied according to FIG. 6C.

$$θ'3 = θ'2 + θ$$
$$= \sin^{-1}(\sin θ1/n) + θ$$

In addition, in the image splitting surface, the following equation is satisfied again according to Snell's Law.

$$n \times \sin θ'3 = \sin θ'4$$

If θ'4 is obtained according to FIG. 6C, the following equation is satisfied $$\theta'4 = \sin^{-1}(n \times \sin\theta'3)$$
$$= \sin^{-1}(n \times \sin(\sin^{-1}(\sin\theta 1/n) + \theta))$$

Further, the emission angle θ2 from the image splitting prism 409 is as follows, $$\theta 2 = \theta'4 - \theta \quad \quad \text{Equation (2)}$$
$$= \sin^{-1}(n \times \sin(\sin^{-1}(\sin\theta 1/n) + \theta)) - \theta.$$

In order to satisfy Equation (1) and Equation (2), an inclination angle θ of the image splitting prism 409 can be obtained from the original object image Y.

Figure 7:
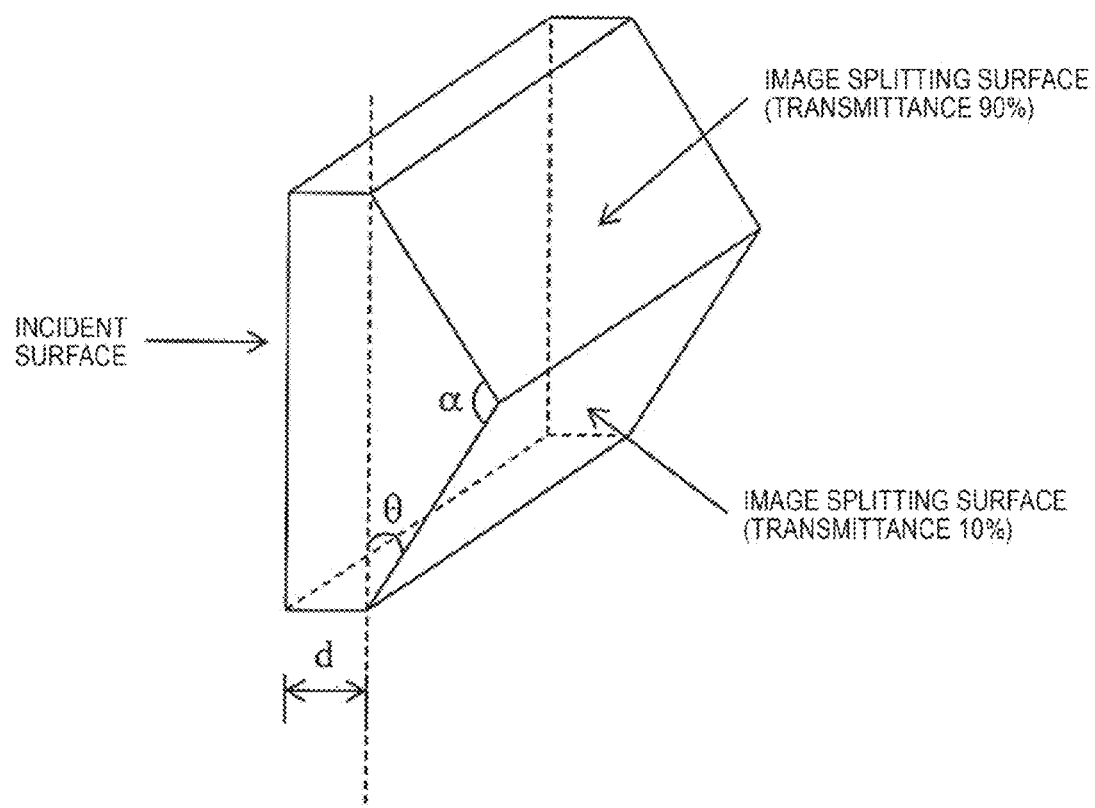
FIG. 7 is a view illustrating a schematic view of the image splitting prism used in Example 1.

FIG. 7 schematically illustrates an image splitting prism 409. The fluorescent light collimated by the condensing lens 403 is incident from the illustrated incident surface. The image splitting prism 409 is configured to include an incident surface as a base and two surfaces inclined by an angle θ from a surface parallel to the incident surface as a split surface. A vertical angle α of the image splitting prism 409 is characterized to be π-2θ. A material of the image splitting prism 409 is, for example, BK7 (refractive index of 1.517).

Figure 8:
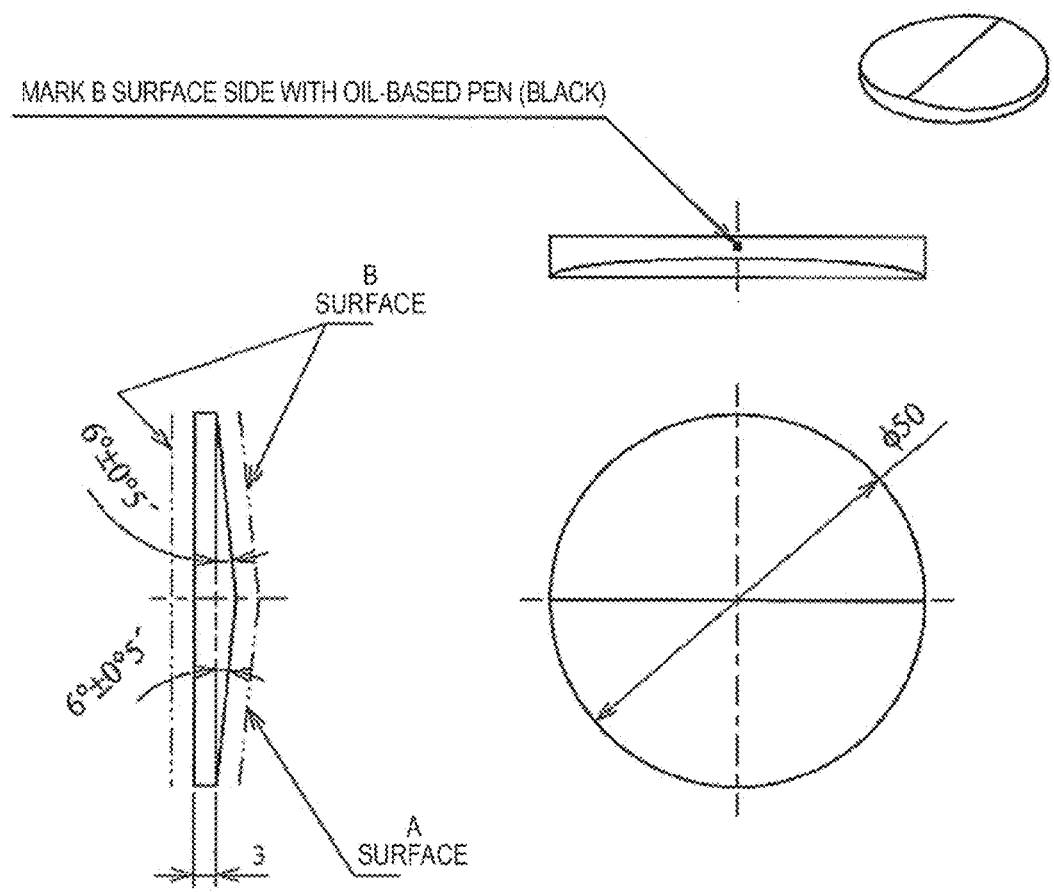
FIG. 8 is a view illustrating a specific example of the image splitting prism used in Example 1.

FIG. 8 illustrates a specific example of the image splitting prism 409. For example, in a case where a capillary array is configured to include 8 capillaries 102, a pitch of the capillary 102 is 363 μm equal to the outer diameter of the capillary, a width of the array is 2.96 mm (=363 μm×8), and the height of the image (object surface) from the center is 1.5 mm, a half of the width. If a focal distance between the condensing lens 403 and the image forming lens 406 is 50 mm, the incidence angle θ1=1.72° and the emission angle μ2=6.47°. The height of the image on the object side is 6.7 mm, which is sufficiently greater than the width of the capillary 2.96 mm, and accordingly, each split image can be obtained on the detector.

In a case where an interval between each capillary is sufficiently great, although not being illustrated (for example, in a case where the interval is equal to or greater than the outer diameter of the capillary), it is possible to capture an image by shifting the first image and the second image by the interval of the capillaries and forming a capillary image of the second image between the capillaries of the first image.

Figure 9A:
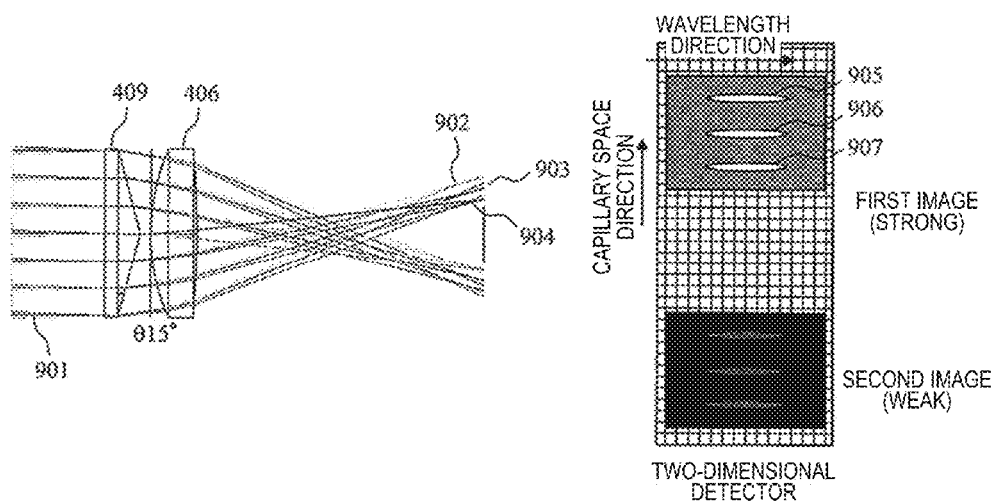
FIG. 9A is a view illustrating a feature of image splitting by a prism of 015°.

FIG. 9A illustrates a view of the light ray tracing in a case where the inclination angle θ of the image splitting prism 409 is 15° and a state of image forming on the two-dimensional detector. For example, in a case where three capillaries 102 are used, three light rays are represented respectively with a subtle angle difference in the light ray tracing (all capillaries) 901. After the image splitting prism 409, the capillaries are split into light ray tracings (first capillary) 902 to (second capillary) 904 of the first image. In the same manner, the light ray tracing of the second image exist in the number of three. The light ray tracing (first capillary) 902 to (second capillary) 904 of the first image and the light ray tracing of the second image reach the two-dimensional detector, and represent capillary images respectively. Since the inclination angle is great, the first image and the second image are obtained by being separated on the two-dimensional detector.

Figure 9B:
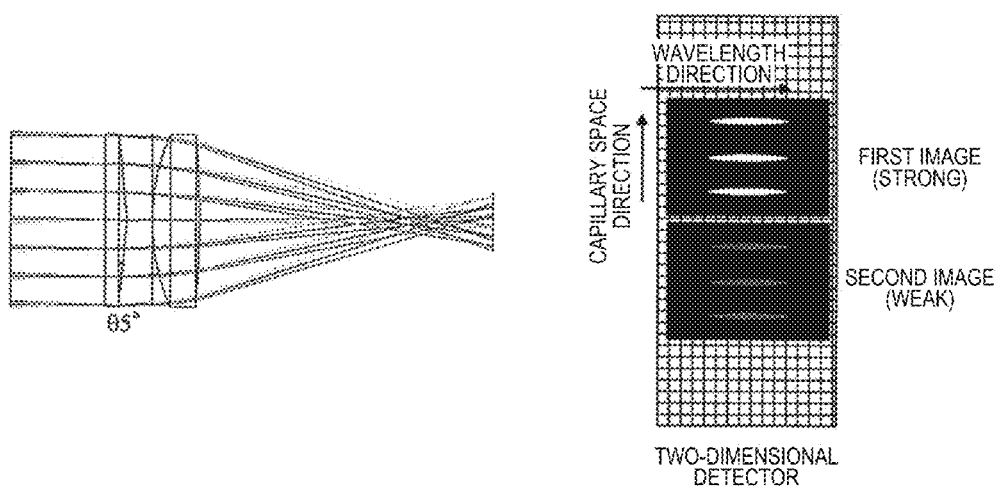
FIG. 9B is a view illustrating a feature of image splitting by a prism of 05°.

Meanwhile, FIG. 9B illustrates a view of the light ray tracing in a case where the inclination angle θ of the image splitting prism 409 is 5° and a state of image forming on the two-dimensional detector. The inclination angle θ is an accurate value with respect to the three capillaries 102, and the first image and the second image are obtained by almost being adjacent to each other on the two-dimensional detector. Therefore, in a case of the present example, if the inclination angle θ of the image splitting prism 409 is set to 5°, an effect is obtained in which a detector region can be used without waste.

In below, the effect will be described using FIG. 10, which is obtained by obtaining two types of strong and weak images having signal intensity in FIG. 4. FIG. 10(a) illustrates an example of the first image (strong) and the second image (weak) formed on the two-dimensional detector. Respectively, a vertical axis represents a space direction of the capillary, that is, a capillary number, and a horizontal axis represents a wavelength scattering direction. Here, the A point (for example, the second capillary, the wavelength of 600 nm) on the two-dimensional detector is focused.

Figures 10A, 10B:
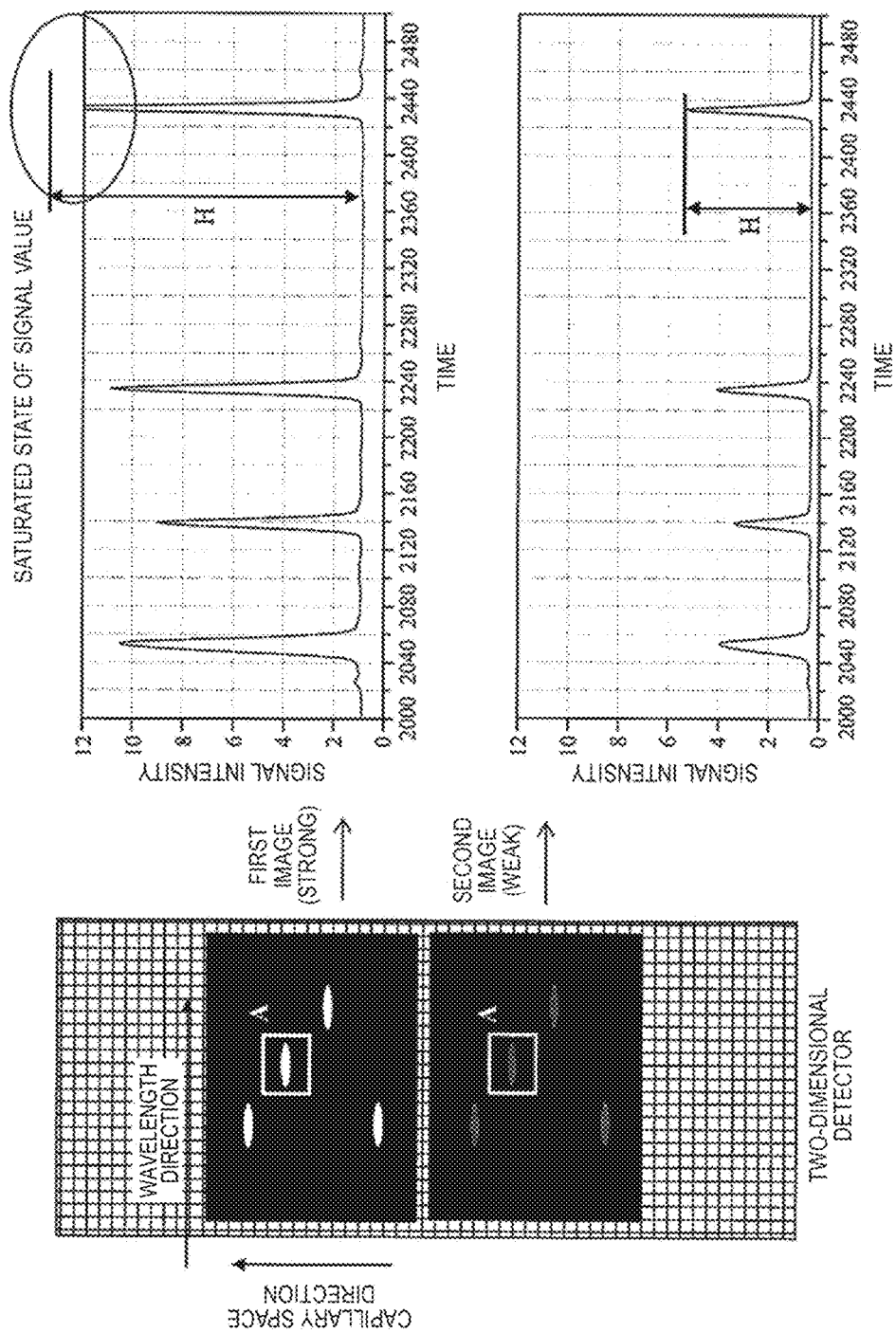
FIGS. 10A and 10B are views illustrating an effect of image splitting by Example 1.

FIG. 10(b) illustrates times series data of each A point in the first image and the second image. A horizontal axis represents time and a vertical axis represents signal intensity. If a DNA fragment flows in, a signal representing the intensity of the fluorescent light emitted by being excited by the laser is detected, and is observed as a time series peak. Normally, since time for which the peak is generated differs depending on the length of the DNA fragment, a plurality of peaks can be observed. In a case where the concentration of the sample is adjusted to an accurate value, normally, all of the DNA fragments can be observed.

Meanwhile, in a case of corresponding to an unknown sample, it is necessary to analyze a DNA fragment having high concentration. At that time, the signal intensity may increase over a saturation limit value ("12" in the drawing) and the accurate value may not be detected. The part indicating "the saturated state of the signal value" of the first image is the above case. Then, if the second image is focused, originally, since the signal intensity is reduced to obtain data, the signal intensity does not exceed the saturation limit value, and data of the same DNA fragment can be obtained. The analysis can be performed more effectively without necessarily performing the analysis again and exemplifying waste of the sample or an analysis cost. By using the first image and the second image differently, the sample having different concentration can be analyzed at once.

The ratio of the signal intensity of the first image to the second image follows the transmittance of each split surface of the image splitting prism. By setting the transmittance to 1:10, it is possible to correspond to the sample having concentration 10 times different from each other. It is possible to determine which one of the first image and the second image to use as a common mode for each apparatus system, and in the present example, data of both images can be obtained. A function for a user of checking the first image and the second image by displaying the images in time series on an operation screen (not illustrated) is provided and accordingly, the user can select the image as well when performing the analysis.

In the present example, two types of the analysis are performed with one detector externally. In the related art, for example, the analysis is performed a plurality of times by changing irradiation detection time or irradiation intensity, which means the same as that the analysis is performed one time with respect to two types of the irradiation detection time (long and short). As such, the fluorescence spectrometer according to the present example functions, as if the analyzer includes two detectors having the same performance or respective parts configuring the apparatus. In other words, externally, a dynamic range of the apparatus is extended, while a SN ratio to be analyzable and sensitivity are retained.

As the above, by extending the dynamic range, the fluorescence spectrometer according to the present example can extremely reduce remeasurement caused by saturation of the measured signal value in the middle of the analysis with respect to the detection range, externally. In particular, when a plurality of samples is simultaneously measured, the measurement can be performed simultaneously even if the concentration of each sample varies greatly. Also, the fluorescence spectrometer is effective for measuring the sample having unknown concentration.

In addition, in the fluorescence detector according to the present example, a plurality of strong and weak detection images can be simultaneously obtained by one detector. Thus, it is possible to provide an apparatus having a small size, a low price, and considerably wide detection range. For example, in a capillary type gene detection apparatus, the dynamic range can be extended 10 or greater times than the related art. Also, by obtaining the plurality of strong and weak detection images simultaneously, the measured points can be retained and highly accurate analysis can be performed.

Example 2

Subsequently, preferred second Example of the fluorescence spectrometer will be described by using a capillary electrophoretic apparatus. In the fluorescence spectrometer in Example 1, the thin prism 409 is used as an image splitting element. The image splitting surfaces of the prism in Example 1 have the equivalent areas (refer to FIG. 4), and by changing the transmittance, the fluorescent intensity of the split image is controlled. However, there is a demerit as follows to vapor-deposit a dielectric multilayer film having different properties on the image splitting surfaces.
1) Since a plurality of vapor-depositing steps is gone through in manufacturing, the cost is high.
2) Decreasing the transmittance causes the amount of light originally condensed to be wasteful.

Figures 11A, 11B:
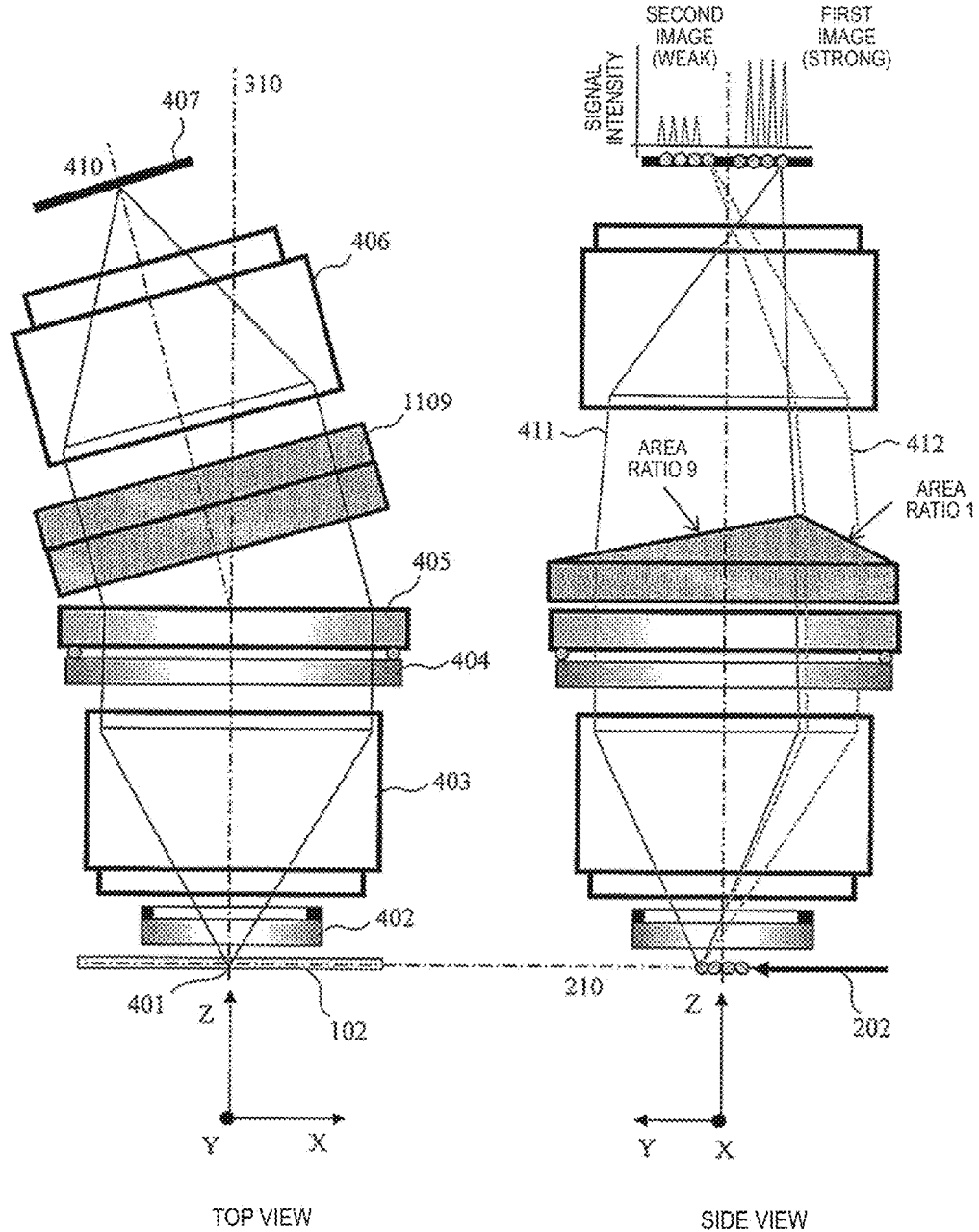
FIGS. 11A and 11B are views illustrating a specific configuration of the fluorescence spectrometer used in Example 2.

Therefore, in Example 2, a prism which controls the fluorescent intensity by the area ratio of the image splitting surface is used. FIG. 11 illustrates a detailed configuration of the fluorescence detector 303 used in the present example. A major configuration is the same as Example 1, but an image splitting prism 1109 having an image splitting surface having a different area ratio is used as an optical element for image splitting.

In the present example, fluorescent light dispersed by the diffraction grating 405 is made to pass through the image splitting prism 1109 having a plurality of image splitting surfaces having a different area, so as to split a plurality of images having different signal intensity by a difference in the area passing through the light. In Example 1, since an optical axis is refracted at the interface of the image splitting surface and air as described using FIG. 6B, a light ray direction of the fluorescent light is changed. The amount of the light ray proportional to the area of the image splitting surface becomes the fluorescent intensity at the time of image forming. That is, the signal intensity to be detected by the two-dimensional detector 407 is determined depending on the area ratio of the image splitting surface.

In a case of FIG. 11, since the area ratio of the two image splitting surfaces of the image splitting prism 1109 is 9:1, two images having the signal intensity of 9:1 can be obtained in the same manner as Example 1. In a case of the fluorescence spectrometer according to the present example, a different dielectric multilayer film does not need to be vapor deposited on the image splitting surfaces, and AR coating with high transmittance may be executed on the entire surfaces. Also, the signal intensity of the two images can be split into 9:1 without losing the original amount of light, and the SN ratio or sensitivity can be retained to be high.

Example 3

Subsequently, preferred third Example of the fluorescence spectrometer will be described by using a capillary electrophoretic apparatus. In the fluorescence spectrometer according to Example 1, a thin prism is used as an image splitting element. However, the prism is one of a wavelength dispersing element and has a function of dispersing a condensed fluorescent light component for each wavelength in the same manner as the diffraction grating. Thus, wavelength dispersing caused by the prism slightly affects in the image splitting direction. Depending on the type of an application or a detection image, a subtle wavelength dispersing may affect the analysis.

Therefore, in the present example, the image splitting element is configured to include a beam splitter (half mirror) and a total reflection mirror. Since an image is split without using a prism, there is no influence by wavelength dispersing caused by the image splitting prism as Example 1 or Example 2.

Hereinafter, a detailed configuration of the fluorescence spectrometer according to Example 3 will be described by referring to FIG. 12. The configuration of the gene analysis apparatus according to Example 3 is the same as the configuration illustrated in FIG. 1. As described above, in the present example, as an image splitting element, a combination structure of an image splitting optical element (for example, a half mirror or a beam splitter) splitting incident light into transmission light and reflection light and the total reflection mirror is used. In below, as the image splitting optical element, a beam splitter 1209 is used.

In a case of the present example, the beam splitter 1209 and a total reflection mirror 1210 are disposed between the condensing lens 403 and the second optical filter 404. As illustrated in FIG. 12, the beam splitter 1209 is disposed at about 45° with respect to the detection optical axis basic axis 310, and the total reflection mirror 1210 is disposed at about 45° or less with respect to the detection optical axis basic axis 310 (for example, 43° to 44°).

The beam splitter 1209 is an optical element having a flat-plate shape and splits the optical path into two by transmission and reflection. In other words, the beam splitter controls the transmittance (or reflectivity) and splits the incident light into two lights at a predetermined split ratio. At the time of splitting, transmission and reflection properties are not different depending on the wavelength as a dichroic mirror, but the transmittance and reflectivity are determined as one in a certain wavelength range. Examples of the type of polarization include a nonpolarized type, an unpolarized type, and a polarized type, but in the present example, a nonpolarized type is used including the polarized state of the incident light.

The fluorescent light of a light emission point 401 is collimated by the condensing lens 403 and is incident to the beam splitter 1209 by an incidence angle of 45°. For example, if the transmittance:reflectivity of the beam splitter 1209 is set to 90%:10%, 90% of the amount of condensed light is transmitted and 10% thereof is reflected. The 90% of light is parallel to the detection optical axis basic axis 310 as shown in the fluorescent light path (strong) 411, dispersed by the diffraction grating 405, and image-formed on the two-dimensional detector 407. Meanwhile, the 10% of reflected light returns substantially parallel to the detection optical axis basic axis 310 by the total reflection mirror 1210 as shown in the fluorescent light path (weak) 412. At this time, the total reflection mirror 1210 is disposed 45° or less (for example, 43° to 44°) with respect to the detection optical axis basic axis 310, and the fluorescent light path (weak) 412 is incident with an angle of 1° to 2°, not completely parallel to the detection optical axis basic axis 310.

Even after the light is dispersed by the diffraction grating 405, the light is image-formed on the two-dimensional detector 407 by the image forming lens 406, while the light has an angle with respect to the detection optical axis basic axis 310. At this time, since the image is formed on a different position from the image formed by the fluorescent light path (strong) 411, two images are formed on the two-dimensional detector 407. The image, which is formed by the fluorescent light path (strong) 411 and in which the condensed light in the amount of 90% is image-formed, has high signal intensity and the image formed by the fluorescent light path (weak) 412 has low signal intensity. The ratio of each signal intensity is 9:1, according to that the transmittance:reflectivity of the beam splitter 1209 is 90%:10%. In the same manner as Example 1, data of two strong and weak types can be obtained.

Here, a cube beam splitter can be used as the beam splitter 1209. There are merits in that the transmission light is not refracted at all, and since a condition of the incidence angle is vertical incidence, light is not necessarily incident at 45° as a plate beam splitter and an alignment becomes easy.

As described above, in the fluorescence spectrometer according to the present example, the fluorescent light condensed by the condensing lens 403 is split into two by the beam splitter 1209, one of the fluorescent light is condensed by the two-dimensional detector 407, and the other fluorescent light is reflected by the total reflection mirror 1210 and then condensed by the two-dimensional detector 407. Since the condensed light image is split into two by the beam splitter 1209, wavelength dispersing does not occur.

Figure 12:
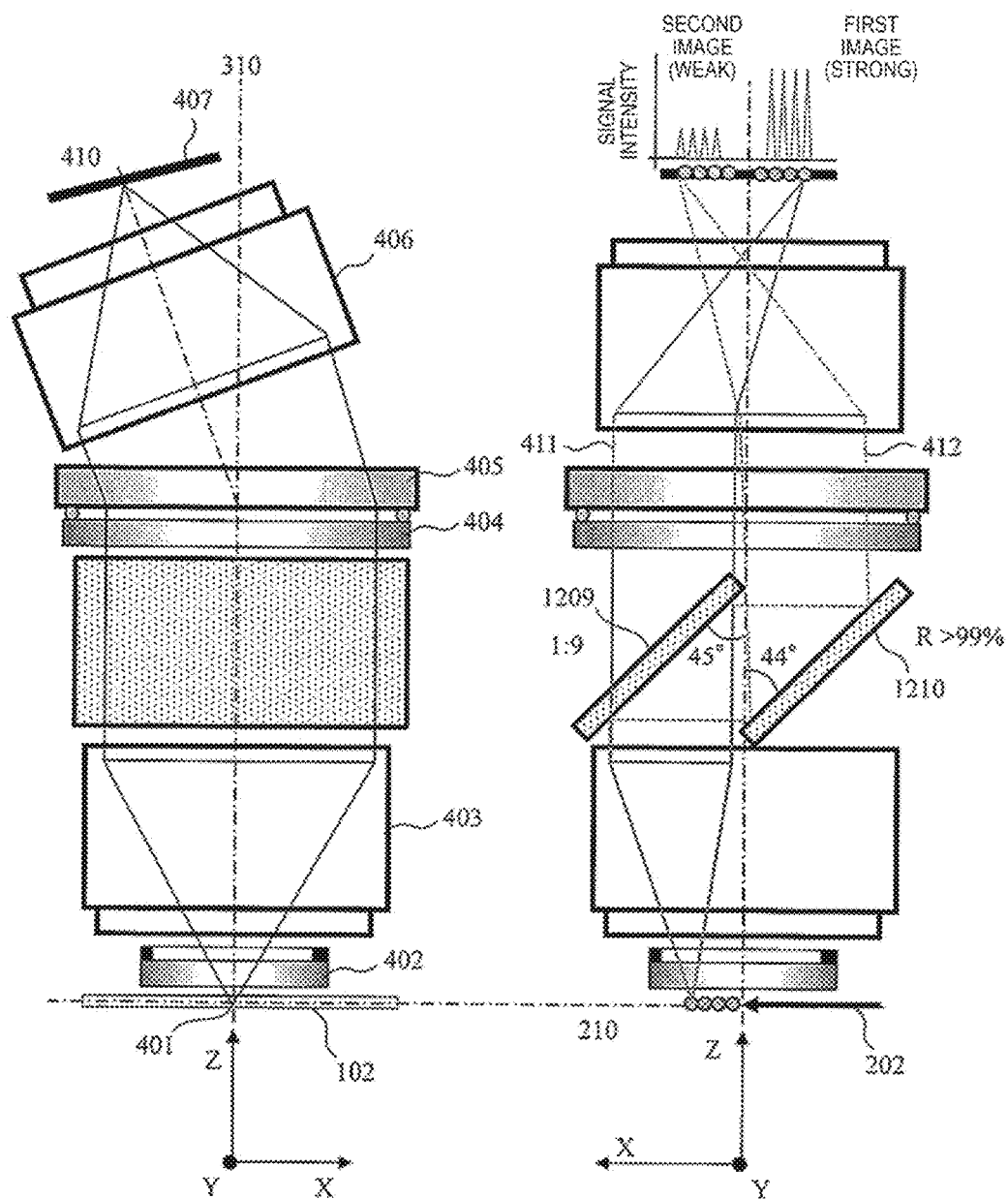
FIG. 12 is a view illustrating a specific configuration of the fluorescence spectrometer used in Example 3.
Figure 13:
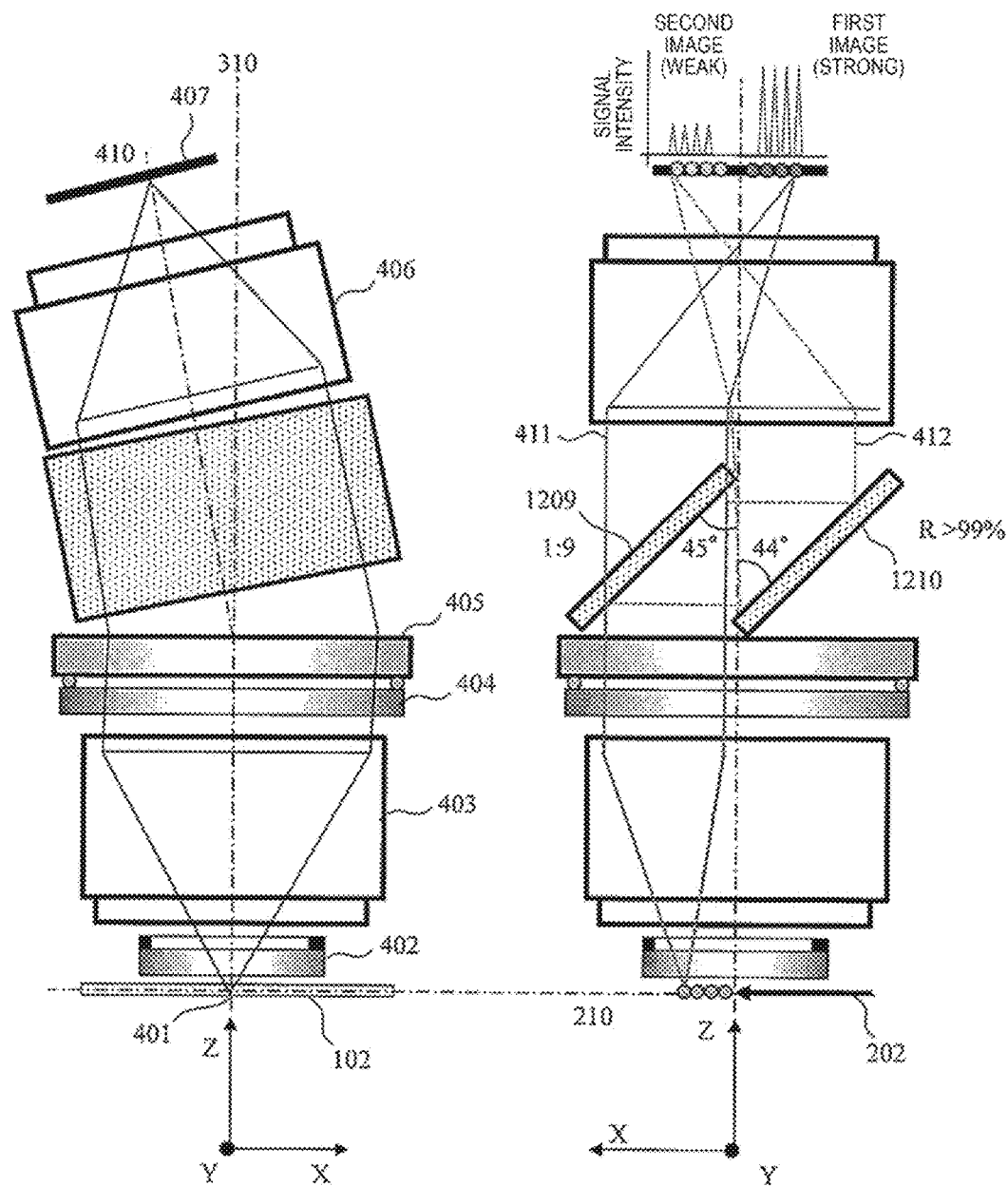
FIG. 13 is a view illustrating a specific configuration of the fluorescence spectrometer used in Example 3.

In addition, the disposition of the optical system configured to include the beam splitter 1209 and the total reflection mirror 1210 is not limited to the disposition illustrated in FIG. 12. For example, as illustrated in FIG. 13, the optical system configured to include the beam splitter 1209 and the total reflection mirror 1210 may be disposed on the detection optical axis after light dispersing 410 between the diffraction grating 405 and the image forming lens 406. In this case, the beam splitter 1209 is disposed at about 45° with respect to the detection optical axis after light dispersing 410. The total reflection mirror 1210 is disposed at about 45° or less (for example, 43° to 44°) with respect to the detection optical axis after light dispersing 410.

Example 4

Subsequently, preferred fourth Example of the fluorescence spectrometer will be described by using a capillary electrophoretic apparatus. In the fluorescence spectrometer according to Examples 1 to 3, the diffraction grating 405 is used as the wavelength dispersing element (light dispersing element). In the present example, an example without using the diffraction grating 405 will be described. Specifically, a method is adopted in which a filter which transmits only a wavelength bandwidth having the highest sensitivity with respect to each fluorescent pigment is rapidly replaced, or a filter which corresponds to an image capturing element in the number of the fluorescent pigment and each of the fluorescent pigment is included to capture an image of each fluorescent element simultaneously. The method of the present example corresponds to that a spectrum in the sample position corresponding to each of the fluorescent pigment is sampled.

Figure 14:
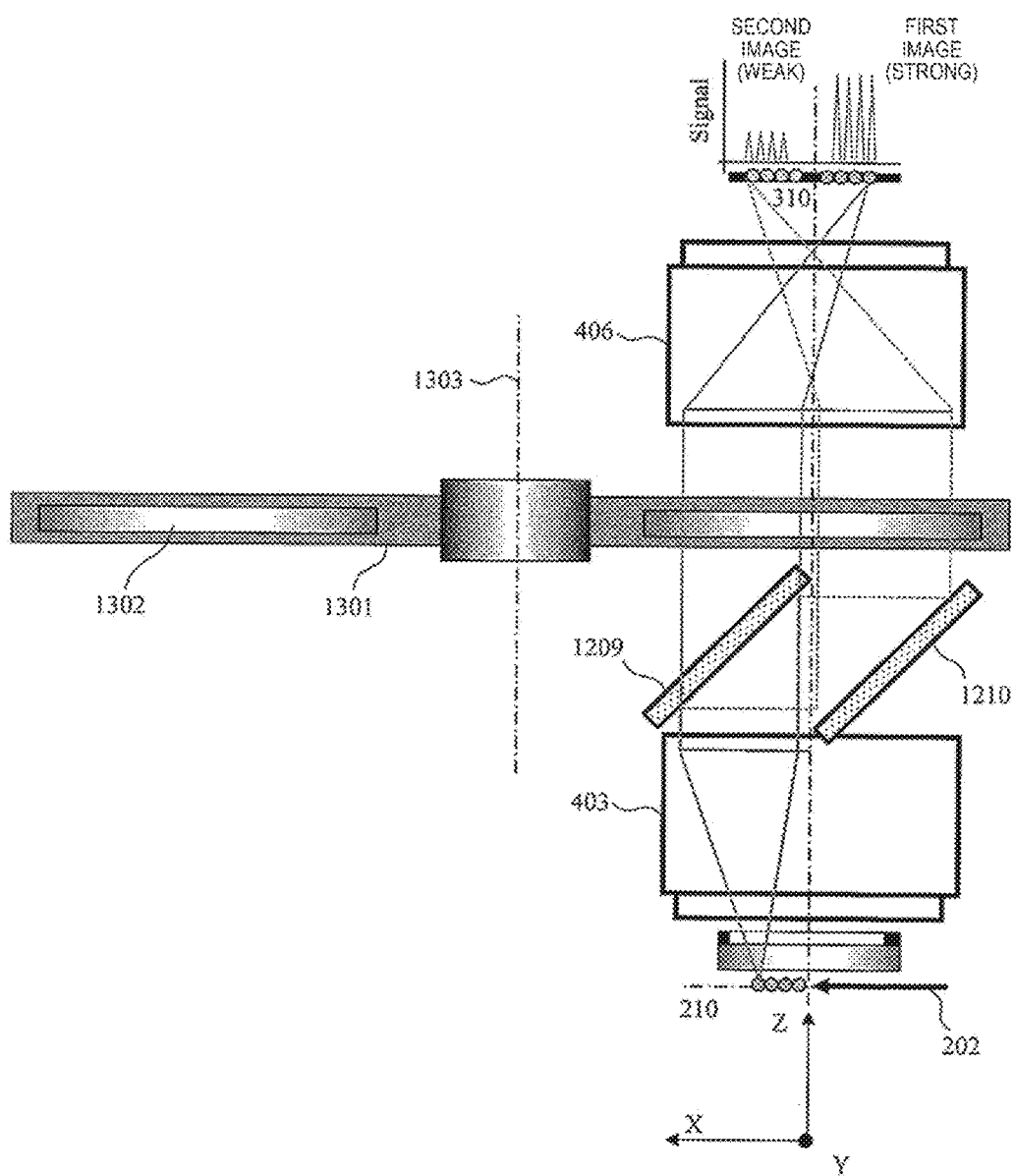
FIG. 14 is a view illustrating a specific configuration of the fluorescence spectrometer used in Example 4.

FIG. 14 illustrates a detailed configuration of the fluorescence detector 303 used in the present example. As illustrated in FIG. 14, the fluorescence detector 303 in the present example includes a filter foil 1301 which rotates rapidly. The filter foil 1301 includes a plurality of fluorescent light filters 1302 which transmit only a wavelength bandwidth having the highest sensitivity with respect to each fluorescent pigment. The fluorescent light filter 1302 is disposed perpendicular to the detection optical axis basic axis 310. In the present example, in the same manner as Example 3, image splitting is performed by the beam splitter 1209 and the total reflection mirror 1210. The split fluorescent light is incident to the fluorescent light filter 1302, dispersed according to the transmission properties of the fluorescent light filter 1302 positioned on the optical path, and image-formed on the two-dimensional detector 407.

In a case of the present example, since light dispersing is performed by exchanging by the fluorescent light filter 1302, not the two-dimensional detector, but one-dimensional line detector can be adopted as the detector. In addition, since the detection region is narrow and the diffraction grating is not used, there is no influence such as image distortion or the like.

Figure 15:
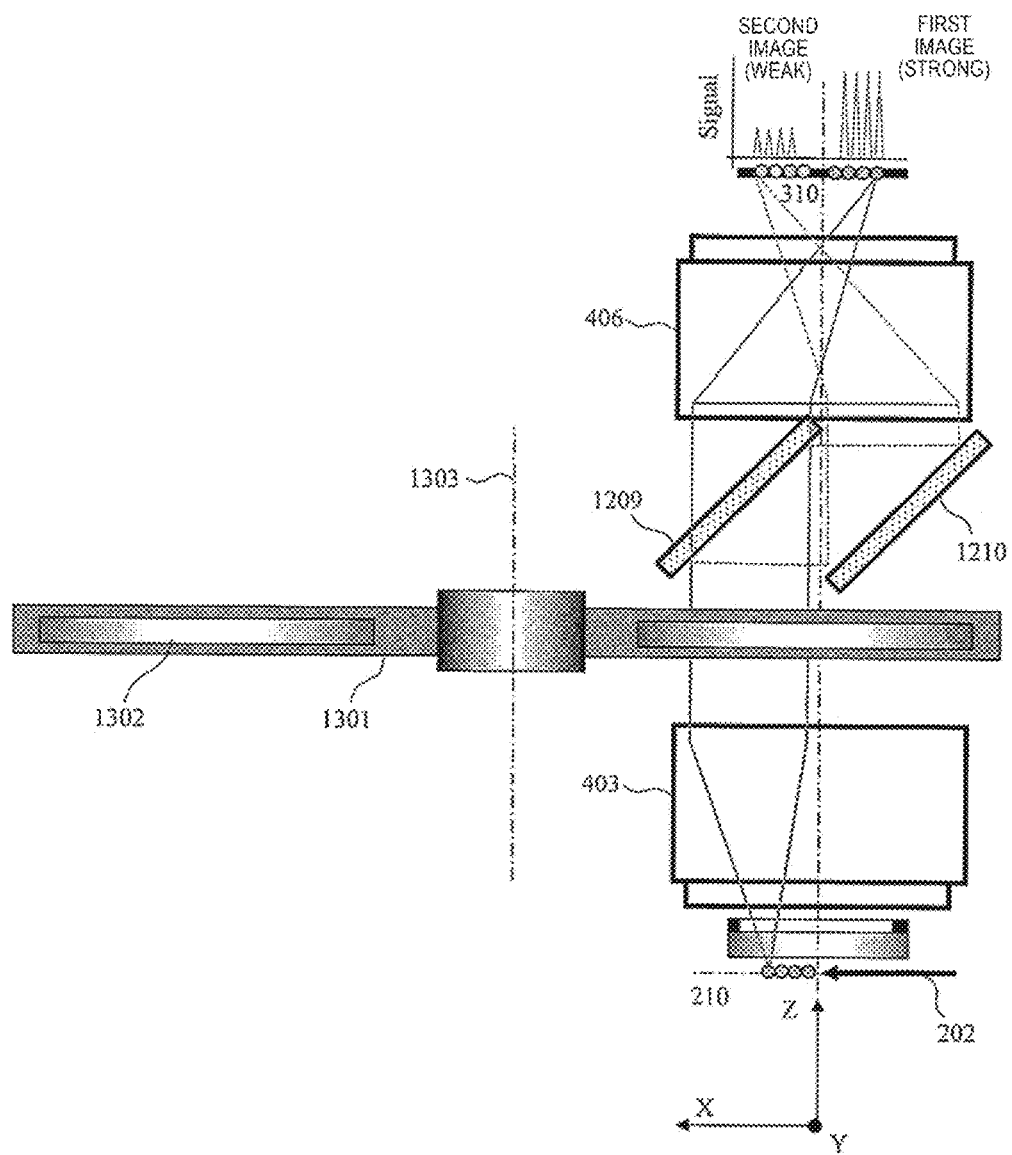
FIG. 15 is a view illustrating a specific configuration of the fluorescence spectrometer used in Example 4.

In addition, even in a case of the present example, the disposition of the optical system configured to include the beam splitter 1209 and the total reflection mirror 1210 is not limited to the disposition illustrated in FIG. 14. For example, as illustrated in FIG. 15, the optical system configured to include the beam splitter 1209 and the total reflection mirror 1210 may be disposed on the detection optical axis after light dispersing 410 between the filter foil 1301 and the image forming lens 406.

OTHER EXAMPLES

In the above, examples of the present invention is described, but the present invention is not limited to these and those skilled in the art understand that various modifications can be made within the scope of the invention described in claims. A combining various examples appropriately is within the scope of the present invention.

REFERENCE SIGNS LIST

100 Gene analysis apparatus
101 Electrophoretic apparatus
102 Capillary
103 Pump mechanism
104 High voltage power supply
105 First ammeter
106 Syringe
107 Block
109 Polymer container
110 Anode buffer container
111 Electrode (GND)
112 Second ammeter 113 Electrically operated valve
114 Light source
115 Optical detector
116 Detection unit
117 Capillary array
118 Thermostatic bath
119 Fan
120 Heating and cooling mechanism
121 Cathode buffer container
122 Cleansing container
123 Waste liquid container
124 Sample container
125 Conveyer
126 Hollow electrode
127 Capillary cathode end.
128 Data analysis apparatus
129 Road header
130 Movable stage
131 Grip
201 Solid-state laser
202 Laser beam
203 Reflecting mirror
204 Polarizer
205 Beam splitter
206 Laser condensing lens
207 Wavelength plate (λ/4)
209 Reference base
210 Irradiation optical axis basic axis
301 Flat plate mask
302 Laser irradiation unit
303 Fluorescence detector
310 Detection optical axis basic axis
401 Light emission point
402 First optical filter
403 Condensing lens
404 Second optical filter
404A Second condensing lens
405 Diffraction grating
406 Imaging lens
407 Two-dimensional detector
409 Thin prism (Image splitting prism)
410 Detection optical axis after light dispersing
411 Fluorescent light path (Strong)
412 Fluorescent light path (Weak)
601 Light ray tracing of the related art
602 Imaging of the related art
603 First light ray tracing
604 Second light ray tracing
605 First imaging
606 Second imaging
901 Light ray tracing (All capillaries)
902 Light ray tracing (first capillary)
903 Light ray tracing (second capillary)
904 Light ray tracing (third capillary)
905 Imaging (first capillary)
906 Imaging (second capillary)
907 Imaging (third capillary)
1109 Image splitting prism (area ratio)
1209 Beam splitter
1210 Total reflection mirror
1301 Filter foil
1302 Fluorescent light filter
1303 Rotation axis of filter

The invention claimed is:

1. A fluorescence spectrometer comprising:
   a light source that irradiates a sample with excitation light;
   a lens that condenses fluorescent light generated from the sample;
   a light dispersing element that causes the condensed fluorescent light to be incident and disperses the light;
   an image splitting element that splits the condensed fluorescent light into a plurality of images having different intensity;
   an image forming element that images the plurality of images in different regions within the same detection plane for specific dispersed light; and
   a detector that simultaneously detects the plurality of images corresponding to different fluorescent intensity in different regions within the same detection plane;
   wherein the image splitting element is disposed between the light dispersing element and the image forming element.

2. The fluorescence spectrometer according to claim 1, wherein the image splitting element is a prism that includes an incident surface that inputs fluorescent light having passed through the light dispersing element; a first light exit surface that transmits a first fluorescent component; and a second light exit surface that transmits a second fluorescent component.

3. The fluorescence spectrometer according to claim 2, wherein a vapor deposited film having different transmittance is respectively formed in the first and second light exit surfaces.

4. The fluorescence spectrometer according to claim 2, wherein at least one of the first and second light exit surfaces is inclined within a range from one to 20 degrees with respect to the incident surface.

5. The fluorescence spectrometer according to claim 2, wherein the detector is a two-dimensional detector.

6. The fluorescence spectrometer according to claim 2, wherein transmittance of the first and second light exit surfaces is different.

7. The fluorescence spectrometer according to claim 2, wherein a ridge which is given as a boundary of the first and second light exit surfaces is disposed in parallel to a migration direction.

8. The fluorescence spectrometer according to claim 2, wherein the light source is a laser, and a ridge which is given as a boundary of the first and second light exit surfaces is disposed perpendicular to a laser emission direction of the laser.

9. The fluorescence spectrometer according to claim 2, wherein a ridge which is given as a boundary of the first and second light exit surfaces is disposed perpendicular to a light dispersing direction.

10. The fluorescence spectrometer according to claim 2, wherein the first and second light exit surfaces have an inclination angle different from each other, and a difference of the inclination angle is from one to 20 degrees.

11. The fluorescence spectrometer according to claim 2, wherein the first and second light exit surfaces have a different area.

12. The fluorescence spectrometer according to claim 1, wherein the image splitting element has a beam splitter that transmits dispersed light input from the light dispersing element at first transmittance and outputs the light to the detector; and a reflection mirror that reflects dispersed light reflected by the beam splitter of the dispersed light input from the light dispersing element and outputs the light to the detector, and the beam splitter and the reflection mirror are arranged in parallel with each other.

13. The fluorescence spectrometer according to claim 12, wherein the detector is a two-dimensional detector.

14. The fluorescence spectrometer according to claim 12, wherein the light dispersing element is a filter mechanism and the detector is a line detector.

15. The fluorescence spectrometer according to claim 1, wherein the image splitting element has a beam splitter that transmits fluorescent light input from the lens at first transmittance and outputs the light to the light dispersing element; and a reflection mirror that reflects a fluorescent component reflected by the beam splitter of the fluorescent light input from the light dispersing element and outputs the component to the light dispersing element.

16. The fluorescence spectrometer according to claim 15, wherein the beam splitter has different values of transmittance and reflectivity.

* * * * *